US010391301B2

(12) United States Patent
Parramon et al.

(10) Patent No.: US 10,391,301 B2
(45) Date of Patent: *Aug. 27, 2019

(54) ARCHITECTURES FOR MULTI-ELECTRODE IMPLANTABLE STIMULATOR DEVICES HAVING MINIMAL NUMBERS OF DECOUPLING CAPACITORS

(71) Applicant: Boston Scientific Neuromodulation Corporation, Valencia, CA (US)

(72) Inventors: Jordi Parramon, Valencia, CA (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/102,302

(22) Filed: Aug. 13, 2018

(65) Prior Publication Data
US 2018/0345007 A1    Dec. 6, 2018

Related U.S. Application Data

(63) Continuation of application No. 15/468,336, filed on Mar. 24, 2017, now Pat. No. 10,071,239, which is a (Continued)

(51) Int. Cl.
*A61N 1/05* (2006.01)
*A61N 1/36* (2006.01)
(Continued)

(52) U.S. Cl.
CPC ............. *A61N 1/05* (2013.01); *A61N 1/3686* (2013.01); *A61N 1/36125* (2013.01); *A61N 1/36185* (2013.01); *A61N 1/37205* (2013.01)

(58) Field of Classification Search
CPC .. A61N 1/05; A61N 1/36125; A61N 1/36185; A61N 1/3686; A61N 1/37205
See application file for complete search history.

(56) References Cited

U.S. PATENT DOCUMENTS 6,035,237 A   3/2000   Schulman et al.
6,125,300 A   9/2000   Weijand et al.
(Continued)

FOREIGN PATENT DOCUMENTS

EP   0985427        3/2000
WO   2008/048321   4/2008

OTHER PUBLICATIONS

Invitation to Pay Additional Fees and, where applicable, Protest Fee from the European Patent Office, regarding corresponding application No. PCT/US2010/028994, dated Jun. 10, 2010.

*Primary Examiner* — Lindsey G Wehrheim
(74) *Attorney, Agent, or Firm* — Lewis & Reese, PLLC

(57) ABSTRACT

Architectures for implantable stimulators having N electrodes are disclosed. The architectures contains X current sources, or DACs. In a single anode/multiple cathode design, one of the electrodes is designated as the anode, and up to X of the electrodes can be designated as cathodes and independently controlled by one of the X DACs, allowing complex patient therapy and current steering between electrodes. The design uses at least X decoupling capacitors: X capacitors in the X cathode paths, or one in the anode path and X-1 in the X cathode paths. In a multiple anode/multiple cathode design having X DACs, a total of X-1 decoupling capacitors are needed. Because the number of DACs X can typically be much less than the total number of electrodes (N), these architectures minimize the number of decoupling capacitors which saves space, and ensures no DC current injection even during current steering.

20 Claims, 22 Drawing Sheets

Related U.S. Application Data continuation of application No. 15/019,402, filed on Feb. 9, 2016, now abandoned, which is a continuation of application No. 12/425,505, filed on Apr. 17, 2009, now abandoned.

(51) Int. Cl.
*A61N 1/368* (2006.01)
*A61N 1/372* (2006.01)
*A61N 1/00* (2006.01)

(56) References Cited

U.S. PATENT DOCUMENTS

| | | |
|---|---|---|
| 6,622,048 B1 | 9/2003 | Mann et al. |
| 7,532,936 B2 | 5/2009 | Erickson et al. |
| 7,941,222 B2 | 5/2011 | Shodo |
| 10,071,239 B2 * | 9/2018 | Parramon .......... A61N 1/36185 |
| 2003/0199955 A1 | 10/2003 | Struble et al. |
| 2005/0245970 A1 | 11/2005 | Erickson et al. |
| 2007/0135868 A1 | 6/2007 | Shi et al. |
| 2007/0239228 A1 | 10/2007 | Bradley |
| 2008/0097529 A1 | 4/2008 | Parramon et al. |

* cited by examiner

ARCHITECTURES FOR MULTI-ELECTRODE IMPLANTABLE STIMULATOR DEVICES HAVING MINIMAL NUMBERS OF DECOUPLING CAPACITORS

CROSS REFERENCE TO RELATED APPLICATIONS

This is a continuation of U.S. patent application Ser. No. 15/468,336, filed Mar. 24, 2017 (allowed), which is a continuation of U.S. patent application Ser. No. 15/019,402, filed Feb. 9, 2016 (abandoned), which is a continuation of U.S. patent application Ser. No. 12/425,505, filed Apr. 17, 2009 (abandoned). These applications are incorporated herein by reference, and priority is claimed to them.

FIELD OF THE INVENTION

The present invention relates generally to multi-electrode implantable stimulator devices.

BACKGROUND

Implantable stimulation devices generate and deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, occipital nerve stimulators to treat migraine headaches, and other neural stimulators to treat urinary incontinence, sleep apnea, shoulder sublaxation, etc. Implantable stimulation devices may comprise a microstimulator device of the type disclosed in U.S. Patent Application Publication 2008/0097529, or a spinal cord stimulator of the type disclosed in U.S. Patent Application Publication 2007/0135868, or other forms.

Microstimulator devices typically comprise a small, generally-cylindrical housing which carries electrodes for producing a desired electric stimulation current. Devices of this type are implanted proximate to the target tissue to allow the stimulation current to stimulate the target tissue to provide therapy. A microstimulator's case is usually on the order of a few millimeters in diameter by several millimeters to a few centimeters in length, and usually includes or carries stimulating electrodes intended to contact the patient's tissue. However, a microstimulator may also or instead have electrodes coupled to the body of the device via a lead or leads.

Some microstimulators 2 in the prior art contain only one or two electrodes, such as is shown in FIG. 1, and are thus referred to as "bi-electrode" microstimulators. An example of a bi-electrode microstimulator device includes the Bion® device made by Boston Scientific Neuromodulation Corporation of Valencia, Calif. A single anode electrode, Eanode, sources current into a resistance R, i.e., the user's tissue. The return path for the current is provided by a single cathode electrode, Ecathode. Either of the anode or cathode electrodes could comprise the case of the device, or other conductive part of the case. Current flows by operation of a current source 20, which typically comprises a Digital-to-Analog Converter, or "DAC" 20, which is programmable to provide a desired therapeutic current, Iout, to the patient's tissue R. Such current Iout is typically pulsed as shown in the bottom of FIG. 1, and can have a frequency and duty cycle suitable for the patient.

A current source or DAC could also be coupled to the anode. However, as shown, the anode is coupled to a compliance voltage, V+, of sufficient strength to provide the current, Iout, programmed into the DAC 20. This compliance voltage can be generated from a battery voltage, Vbat, provided by a battery 12 in the microstimulator 2. A DC-DC converter 22 is used to boost Vbat to the desired compliance voltage V+, and is controlled by a V+ monitor and adjust circuitry 18. Because such circuitry for compliance voltage generation is well known, and not directly germane to the issues presented by this disclosure, further elaboration is not provided.

Also shown in FIG. 1 is the provision of decoupling or blocking capacitors 42 and 44 hardwired to the anode and cathode respectively. As is well known, such decoupling capacitors only allow the passage of AC components of the current provided by the DAC 20, and thus prevent the DC injection of current into the patient's tissue R (Idc=0). Preventing DC current injection into the tissue is desired for safety: when the DC component of the current is removed, the possibility of current building up in the patient's tissue is minimized.

Although two decoupling capacitors 42 and 44 are shown in FIG. 1, only one is needed to prevent DC current injection, which one capacitor is coupled to the DAC 20. Thus, when the DAC 20 appears on the cathode side of the current path, only a cathode capacitor 44 is needed, as shown in FIG. 2. Likewise, were the DAC 20 on the anode side of the current path, only an anode capacitor 42 would be needed (not shown in FIG. 2). Using only one decoupling capacitor 42 or 44 is preferred because the decoupling capacitors tend to be rather large in comparison to the rest of the circuitry within the microstimulator 2, and hence take up significant room in the case. Reducing the number of decoupling capacitors therefore allows the microstimulator 2 to be made smaller, which simplifies the implanting procedure and conveniences the patient.

Bi-electrode microstimulators 2 benefit from simplicity. Because of their small size, such microstimulators 2 can be implanted at site requiring patient therapy, and without leads to carry the therapeutic current away from the body as mentioned previously. However, such bi-electrode microstimulators lack therapeutic flexibility: once implanted, the single cathode/anode combination will only recruit nerves in their immediate proximity, which generally cannot be changed unless the position of the device is manipulated in a patient's tissue.

To improve therapeutic flexibility, microstimulators having more than two electrodes have been proposed, and such devices are referred to herein as "multi-electrode" microstimulators to differentiate them from bi-electrode microstimulators discussed above. When increasing the number of electrodes in this fashion, the electrodes can be selectively activated once the device is implanted, providing the opportunity to manipulate therapy without having to manipulate the position of the device.

Exemplary multi-electrode microstimulators 4, 6, and 8 are shown in FIGS. 3A-3C respectively, and are disclosed in the '529 Publication referenced above. As its name suggests, the multi-electrode microstimulator comprises a plurality of electrodes, which electrodes may be located on the case in various manners, such as on two sides of the case as shown in the pictures at the bottom right of FIGS. 3A-3C. In this and subsequent examples, it should be noted that any of the electrodes can comprise the implant's case, or conductive portions thereof.

In the embodiment of FIG. 3A, there is provided a dedicated anode electrode, Eanode. By contrast, one of E1 cathode-Encathode is selectable as the cathode via cathode switches $62_1$-$62_g$. Selecting a particular cathode by closing its corresponding cathode switch couples that cathode to the DAC 20. For example, FIG. 3A shows the circuit that is completed when E1 cathode is selected. Notice that this design employs a single decoupling capacitor 42 in the anode path.

Also shown in FIG. 3A are recovery switches 64 and $66_1$-$66_n$. As explained in the above-referenced '529 Publication, the recovery switches 64 and $66_1$-$66_n$ are activated at some point after provision of a stimulation pulse, and have the goal of recovering any remaining charge left on the decoupling capacitor 44 and in the patient's tissue. Thus, after a stimulation pulse, the recovery switch 64 and at least one of switches $66_1$-$66_n$ are closed. Closure of these switches places the same reference voltage on each plate of the decoupling capacitor 302, thus removing any stored charge. In one embodiment, for convenience, the reference voltage used is the battery voltage, Vbat, of the battery in the microstimulator 4, although any other reference potential could be used. Thus, during recovery, Vbat is placed on the left plate of capacitor 44 via recovery switch 64, and is likewise placed on the right plate (through the patient's tissue, R) via one or all of the recovery switches $66_1$-$66_n$. As recovery is discussed in further detail in the '529 Publication, and it is not directly germane to this disclosure, it is not further discussed.

The embodiment of FIG. 3B improves upon the embodiment of FIG. 3A in that it allows the anode electrode to be selected as well as the cathode electrode. Thus, the device contains N electrodes, E1-En, any of which can comprise the anode or cathode at any given time. As before, which electrode acts as the cathode is determined by selecting a particular cathode switch $62_1$-$62_n$. Which electrode acts as the anode is determined by selecting a particular anode switch $68_1$-$68_n$. For example, FIG. 3B shows the circuit that is completed when E1 is selected as the anode, and E2 is selected as the cathode. Notice again that this design employs a single decoupling capacitor 42 in the anode path, regardless of which electrode is selected as the anode.

The embodiments of FIGS. 3A and 3B are similar in that the singular decoupling capacitor 42 prevents DC current injection to the patient's tissue R, i.e., Idc=0. As a result, these designs can be regarded as generally safe for the reasons stated earlier. Moreover, these designs are generally compact: most significantly, they only require a single decoupling capacitor 42.

However, the designs of FIGS. 3A and 3B have a shortcoming arising from their provision of a single DAC 20, namely the inability to simultaneously and independently modify the current at two or more different cathodes. Being able to so modify the current at two (or more) different cathode electrodes is desired in one example to "steer" current from one cathode to another. The concept of current steering is addressed in U.S. Patent Application Publication 2007/0239228, and so is only briefly explained here with reference to FIG. 4. FIG. 4 presents an initial condition, in which E2 has been designated as the anode, and E4 has been designated as the cathode. As the net amount of current provided by these electrodes must equal zero, E2 sources 10 mA, while E4 sinks −10 mA. In the next condition, some of the sink current (−2 mA) has been moved or "steered" from cathode electrode E4 to E3. Steering in 2 mA increments continues until in the last condition, all of the sink current (−10 mA) has been moved to cathode E3, while original cathode E4 is now off. Anode current can be similarly steered in some stimulators, but this is not shown. Being able to steer the current in this fashion not only improves the complexity of therapy that can be provided to the patient, but also allows for safe and comfortable experimentation during fitting to determine the best electrodes to activate for a particular patient. However, the designs of FIGS. 3A and 3B cannot so steer the current at two different cathodes simultaneously.

An embodiment disclosed in the above-referenced '529 Publication capable of current steering is shown in FIG. 3C. This microstimulator 8 improves from the microstimulator 6 of FIG. 3B in that each electrode E1-En has its own dedicated, and independently-controllable, DAC $20_1$-$20_n$. As a result, more than one electrode can be selected as the cathode at any given time via selection of two or more of the cathode selection switches $62_1$-$62_n$, and the current sunk at each can be independently controlled by the corresponding DACs $20_1$-$20_n$, which enables current steering of the sort depicted in FIG. 4.

Unfortunately, microstimulator 8 of FIG. 3C has a shortcoming related to its provision of a single decoupling capacitor 42, namely the possibility of direct DC current injection into the patient's tissue R during current steering. This is illustrated in FIG. 5. The first circuit shows the selection of Ex as the anode, and only a single electrode Ey as the cathode. In this condition, the decoupling capacitor 42 prevents DC current injection through the entirety of the current path. However, the second circuit shows the selection of electrodes Ey and Ez as cathodes, such as might occur when some of the current at Ey is steered to Ez. In this configuration, the decoupling capacitor 42 prevents DC current injection in the anode path $Idc_a$=0. However, no such decoupling capacitor appears in the cathode paths, and therefore DACs 20y and 20z are not prevented from providing a DC current through the patient's tissue. In short, while the design of FIG. 3C allows for current steering, and might be relatively compact by virtue of its single capacitor 42, it does not guarantee an absence of direct DC current injection into each cathode electrode.

FIG. 6 provides yet another design for a multi-electrode implantable stimulator 10. This type of design is often used in a spinal cord stimulator (SCS), such as that illustrated in the above-referenced '868 application. An SCS 10 will typically have a case which is coupled by leads to an electrode array. The electrode array is implanted into the patient's spine, while the case is implanted at a distant, less-critical location, such as in the patient's buttocks. Because the case is not implanted right at the location requiring stimulation, the case of the SCS 10 can typically be larger than the various microstimulators illustrated to this point.

As seen in FIG. 6, the SCS 10 has a plurality of electrodes E1-En. Hardwired to each electrode are decoupling capacitors C1-Cn, and coupled to each of these capacitors are DACs $20_1$-$20_n$. In this particular design, the DACs can be controlled to operate as either current sources or current sinks, and thus their associated electrodes can comprise anodes or cathodes. Shown in FIG. 6 is an example in which DAC $20_2$ is active as a source thus designating E2 as an anode, and DAC $20_4$ is active as a sink thus designating E4 as a cathode. All other DACs, and their associated electrodes, are inactive.

Because the SCS 10 has individually-controllable DACs dedicated to each of the electrodes, current can readily be steered between the two electrodes. That is, two or more of the electrodes can act as cathodes (sinks) and/or two or more of the electrodes can act as anodes (sources) at one time. Moreover, because each electrode is hardwired to a decoupling capacitor C1-Cn, there is no risk of direct DC current injection into the tissue R of the patient, even during current steering.

The SCS 10 system therefore has many favorable functional benefits. However, the requirement that each of the N electrodes be hardwired to a dedicated decoupling capacitor means that N decoupling capacitors must be provided. As mentioned before, these capacitors can take up significant space in the case of the implantable stimulator. This may not be as critical of a concern where the implantable stimulator is an SCS 10 for example, because as mentioned, that type of device can generally support a larger case. However, where a small-sized microstimulator is concerned, the requirement of N capacitors for each of the N electrodes is prohibitive.

Accordingly, the inventor believes that the implantable stimulator art, and particularly the multi-electrode microstimulator art, would benefit from an architecture that would minimize device size and ensure patient safety. Specifically desirable would be a design that would minimize the number of decoupling capacitors required, but which would still prevent DC current injection even during current steering. Embodiments of such a solution are provided herein.

DETAILED DESCRIPTION

Architectures for implantable stimulators having N electrodes are disclosed. The architectures contains X current sources, or DACs. In a single anode/multiple cathode design, one of the electrodes is designated as the anode, and up to X of the electrodes can be designated as cathodes and independently controlled by one of the X DACs, allowing complex patient therapy and current steering between electrodes. The design uses at least X decoupling capacitors: X capacitors in the X cathode paths, or one in the anode path and X−1 in the X cathode paths. In a multiple anode/multiple cathode design having X DACs, a total of X−1 decoupling capacitors are needed. Because the number of DACs X can typically be much less than the total number of electrodes (N), these architectures minimize the number of decoupling capacitors which saves space, and ensures no DC current injection even during current steering.

Figure 6:
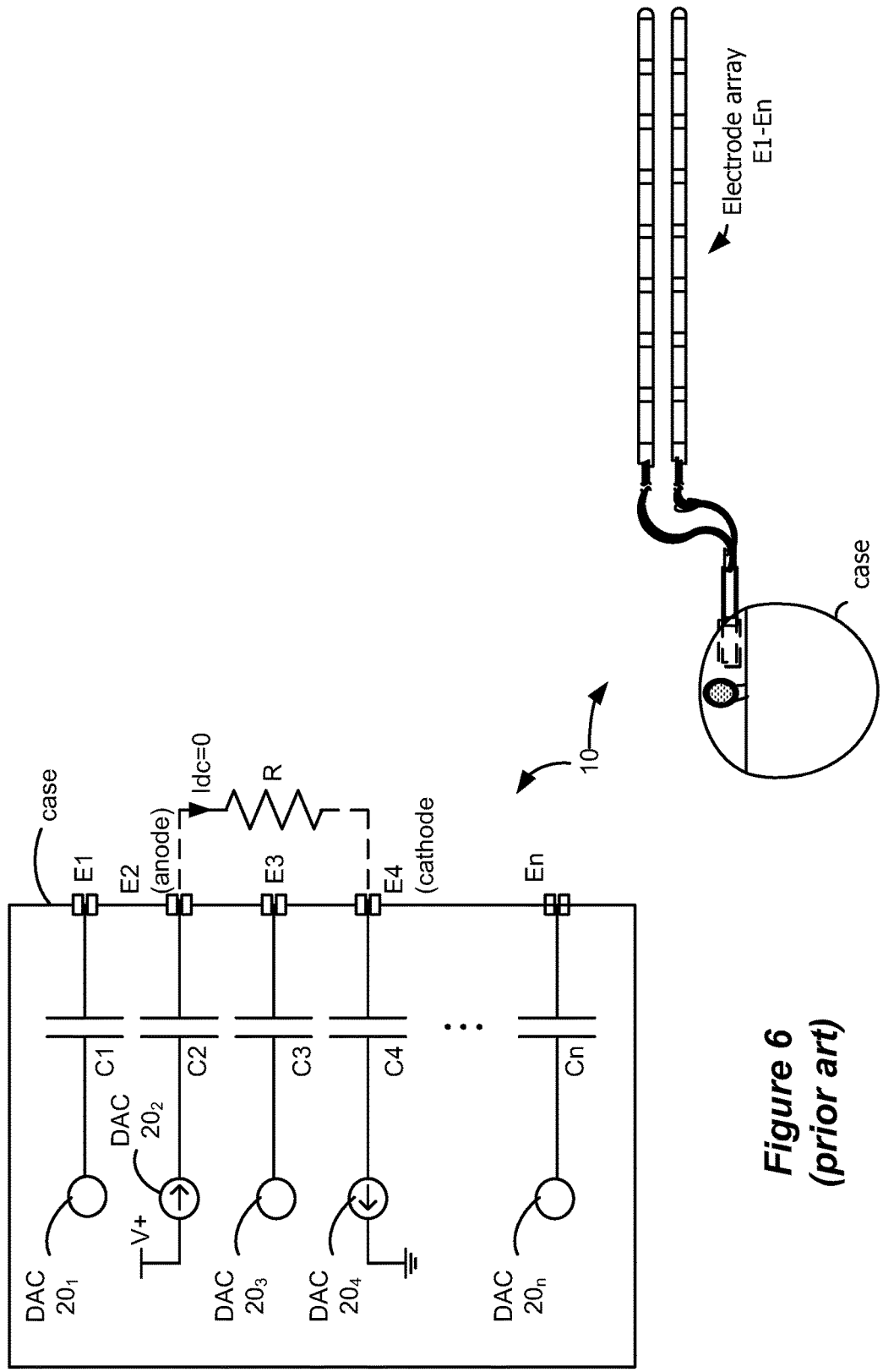
FIG. 6 illustrates the basic electrical components of a spinal cord stimulator in accordance with the prior art.
Figure 7A:
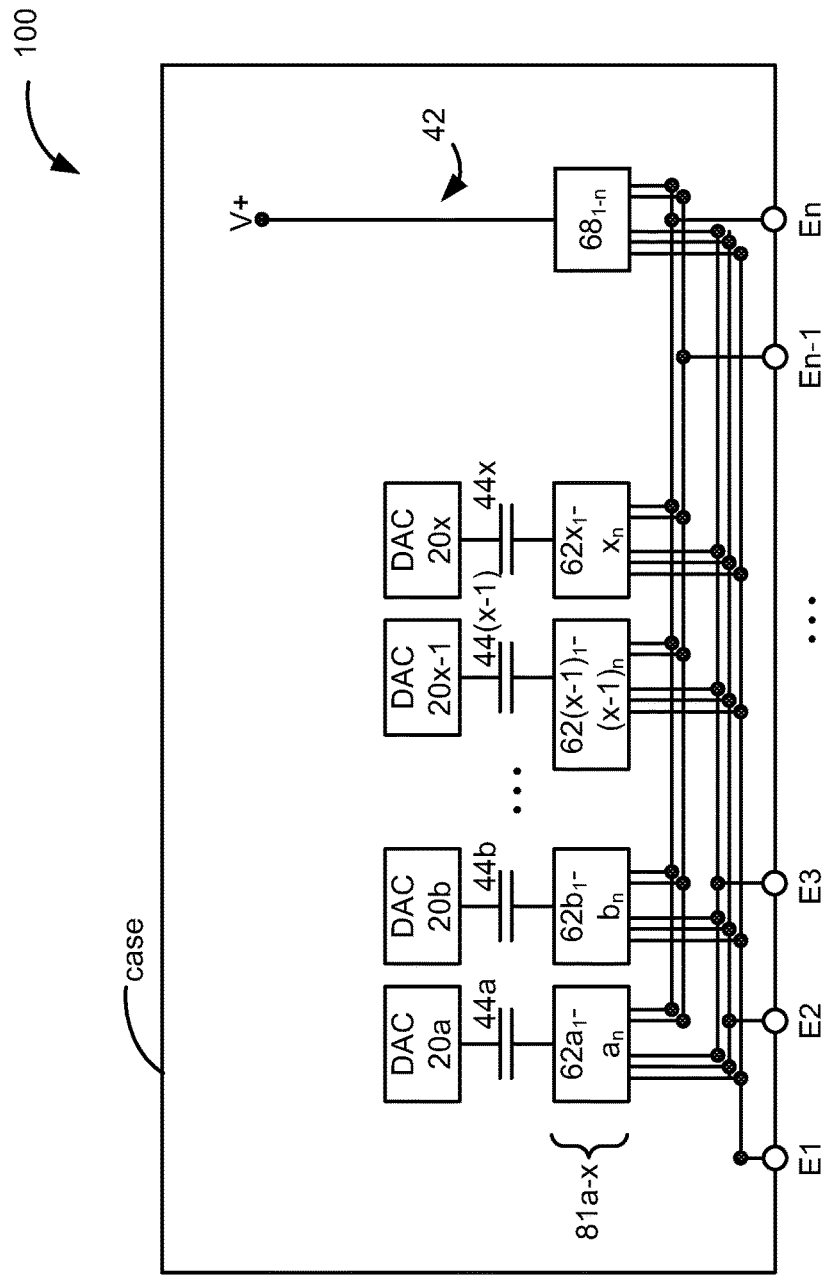
FIGS. 7A-7C illustrate a single anode/multiple cathode stimulator having a minimal number of decoupling capacitors in accordance with an embodiment of the invention.
Figure 7B:
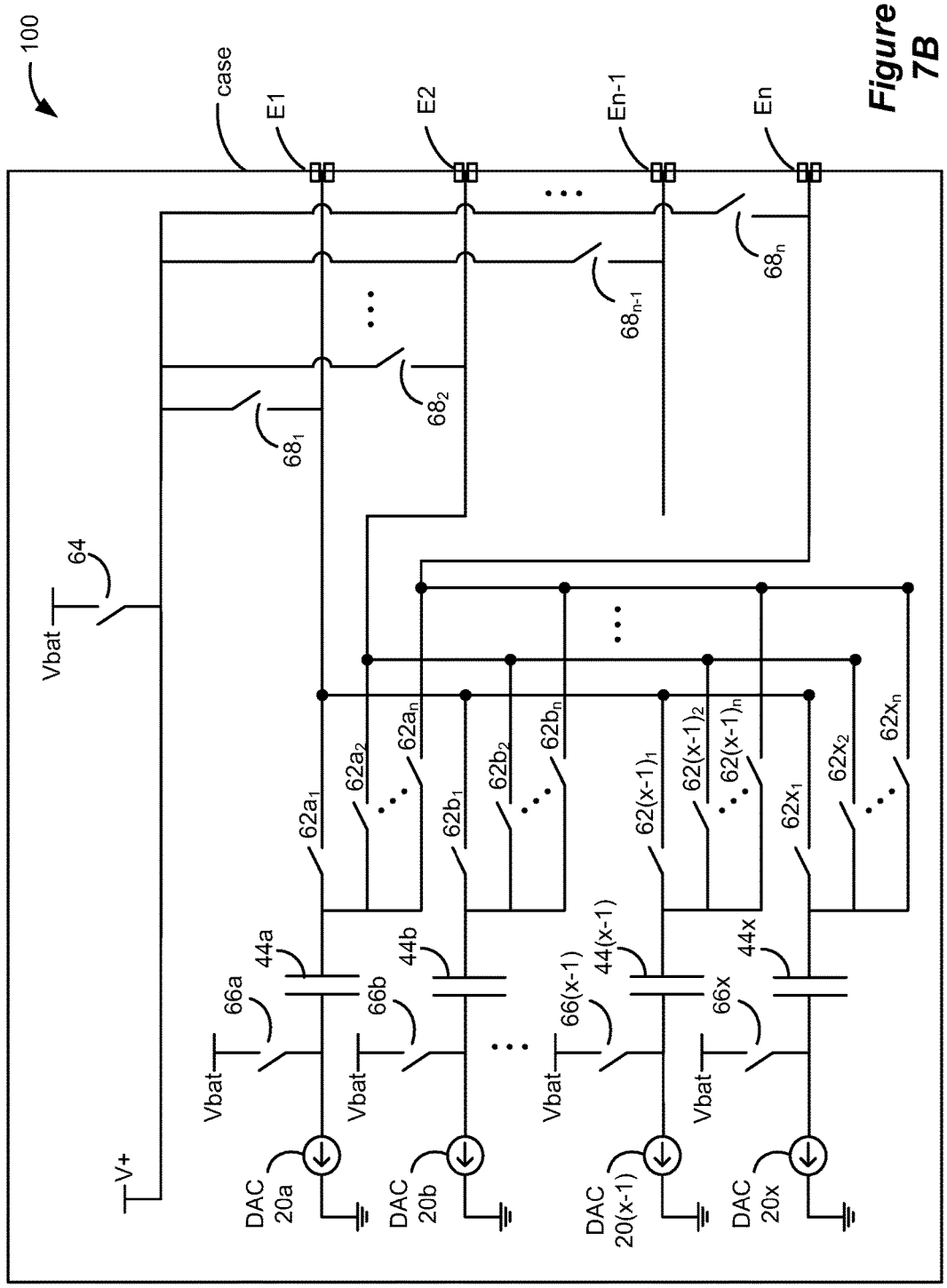
Figure 8A:
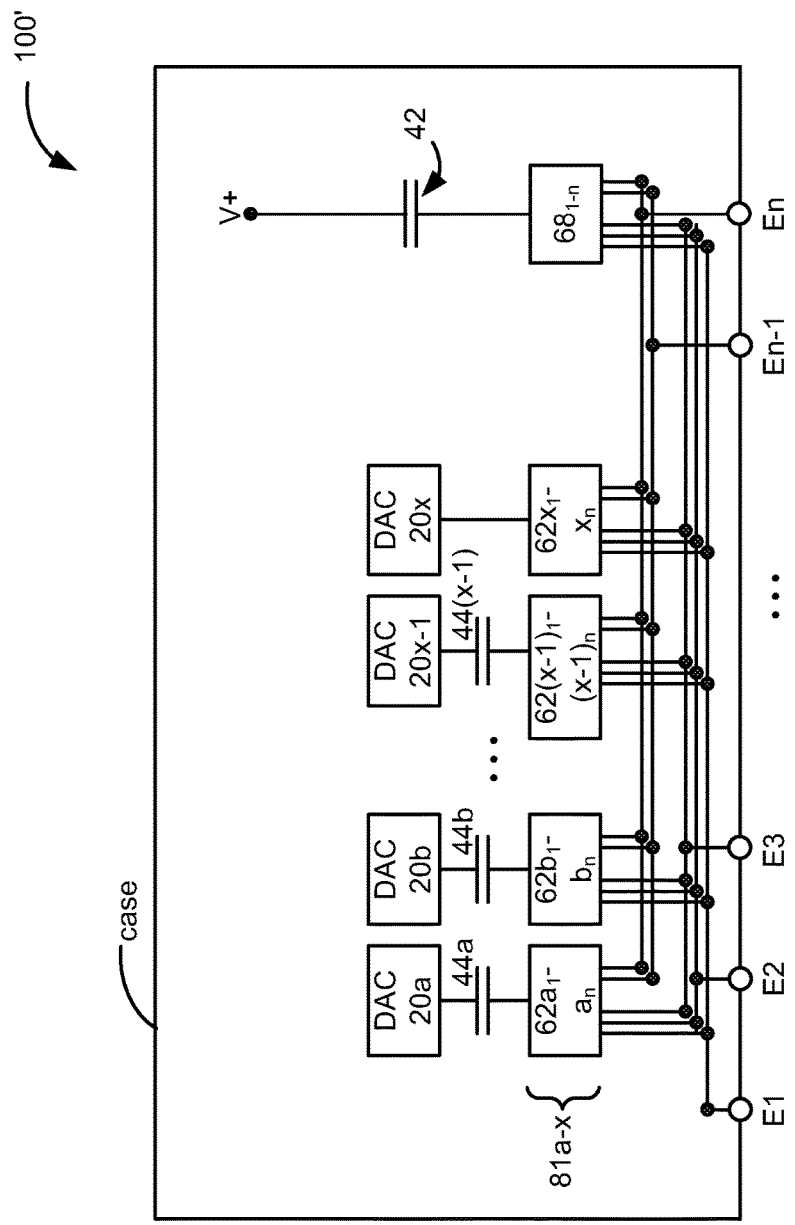
FIGS. 8A-8D illustrate another single anode/multiple cathode stimulator having a minimal number of decoupling capacitors in accordance with an embodiment of the invention.
Figure 8B:
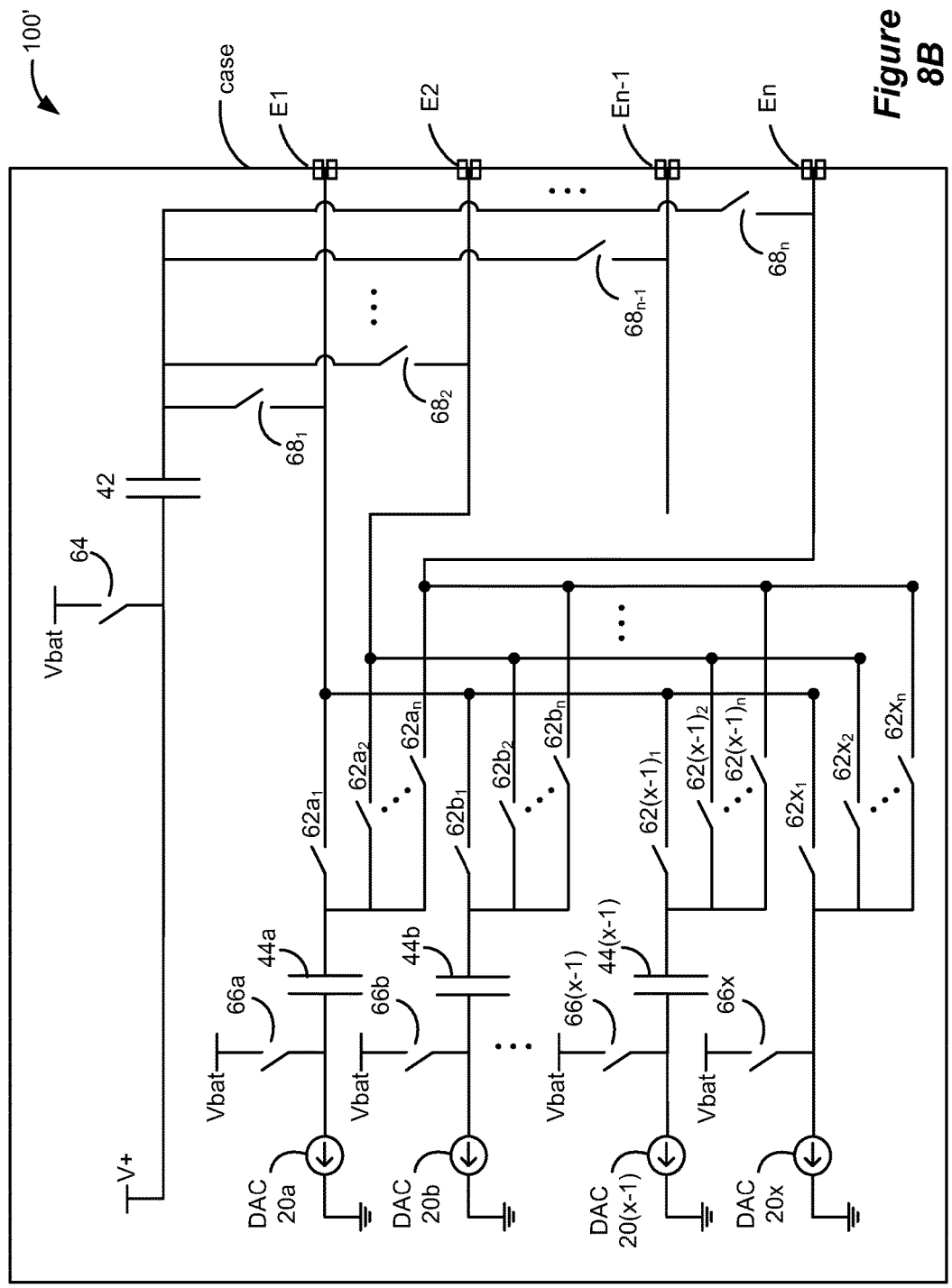

A first embodiment of an improved multi-electrode stimulator 100 is shown in FIGS. 7A and 7B, and a second embodiment 100' is shown in FIGS. 8A and 8B. The stimulators 100 and 100' comprise single anode/multiple cathode stimulators similar to microstimulator 8 illustrated earlier in FIG. 3C. However, stimulators 100 or 100' could also be employed in a spinal cord stimulator 10 similar to that illustrated in FIG. 6, or in any other implantable stimulator.

Figure 1:
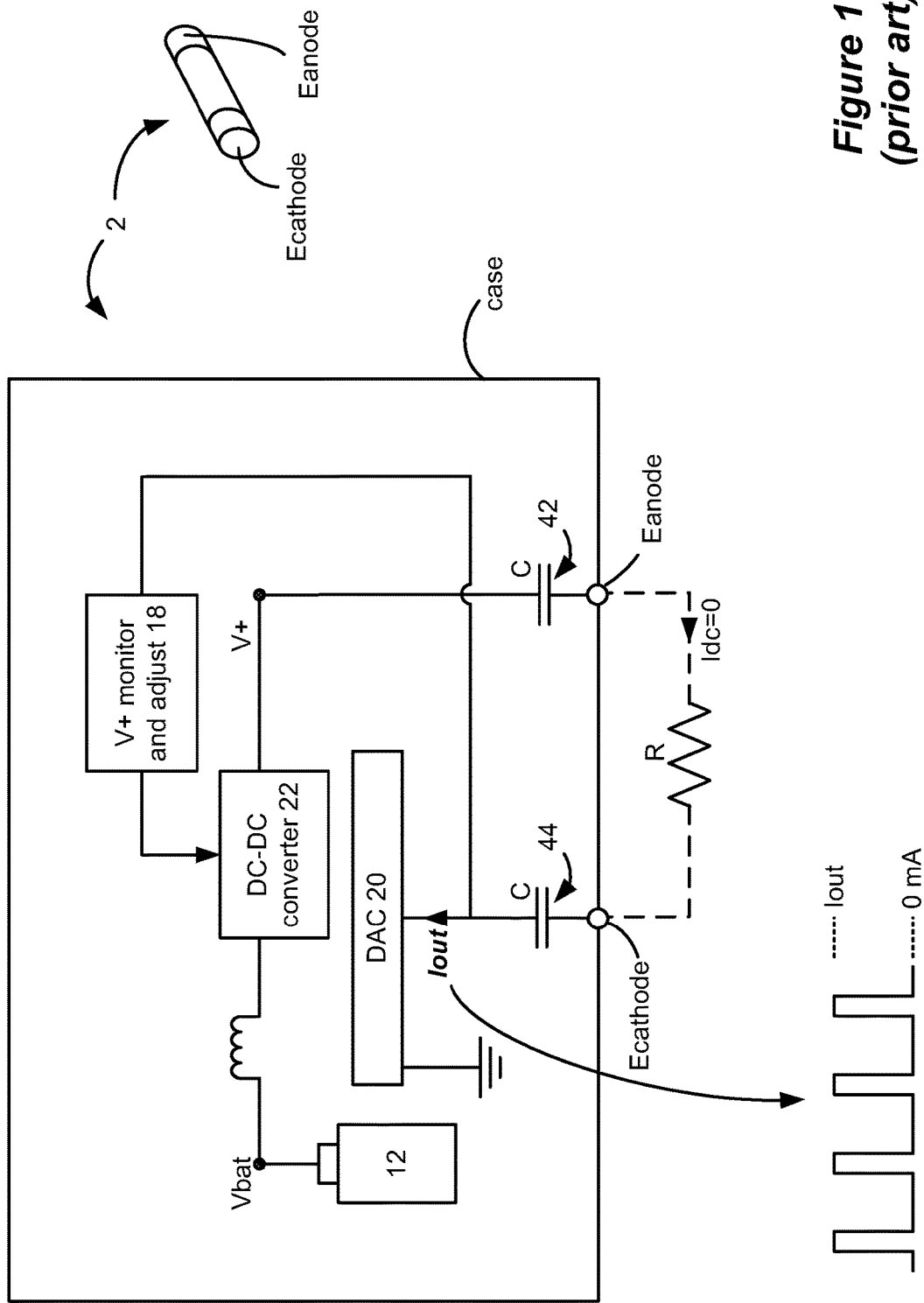
FIGS. 1 and 2 illustrate the basic electrical components of a bi-electrode microstimulator in accordance with the prior art.
Figure 2:
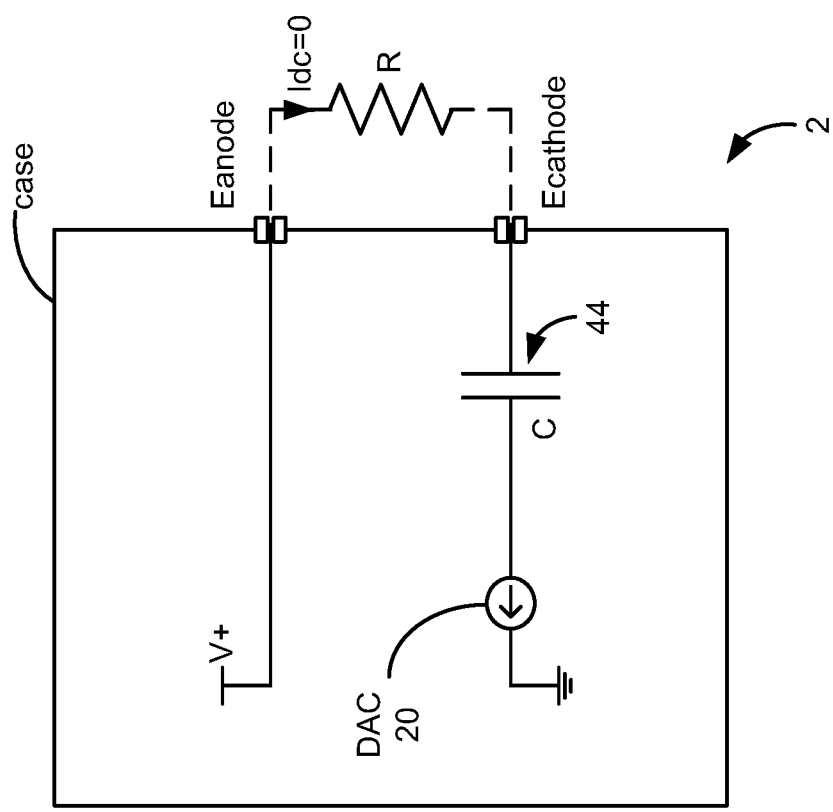
Figure 3A:
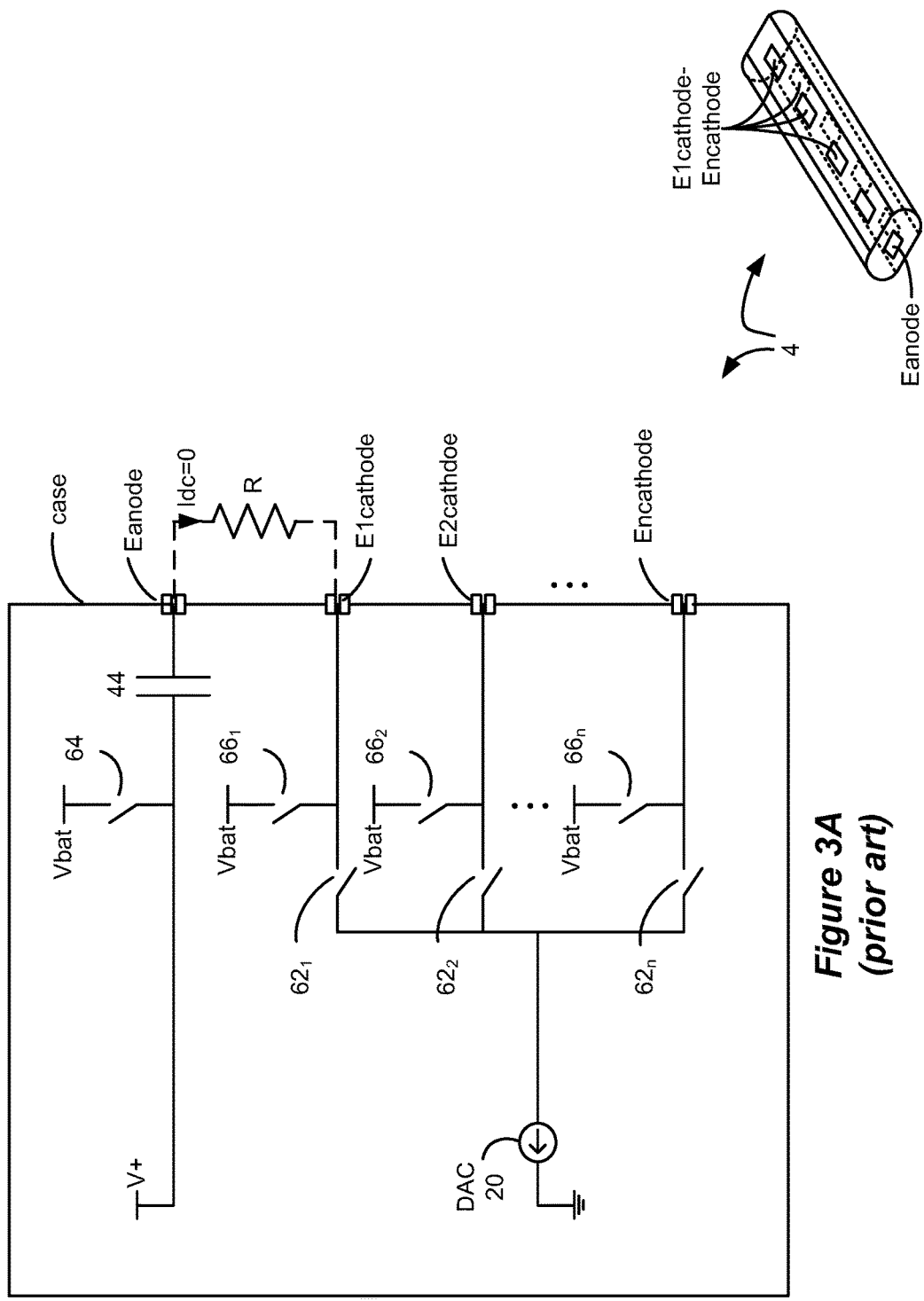
FIGS. 3A through 3C illustrate the basic electrical components of multi-electrode microstimulators in accordance with the prior art.
Figure 3B:
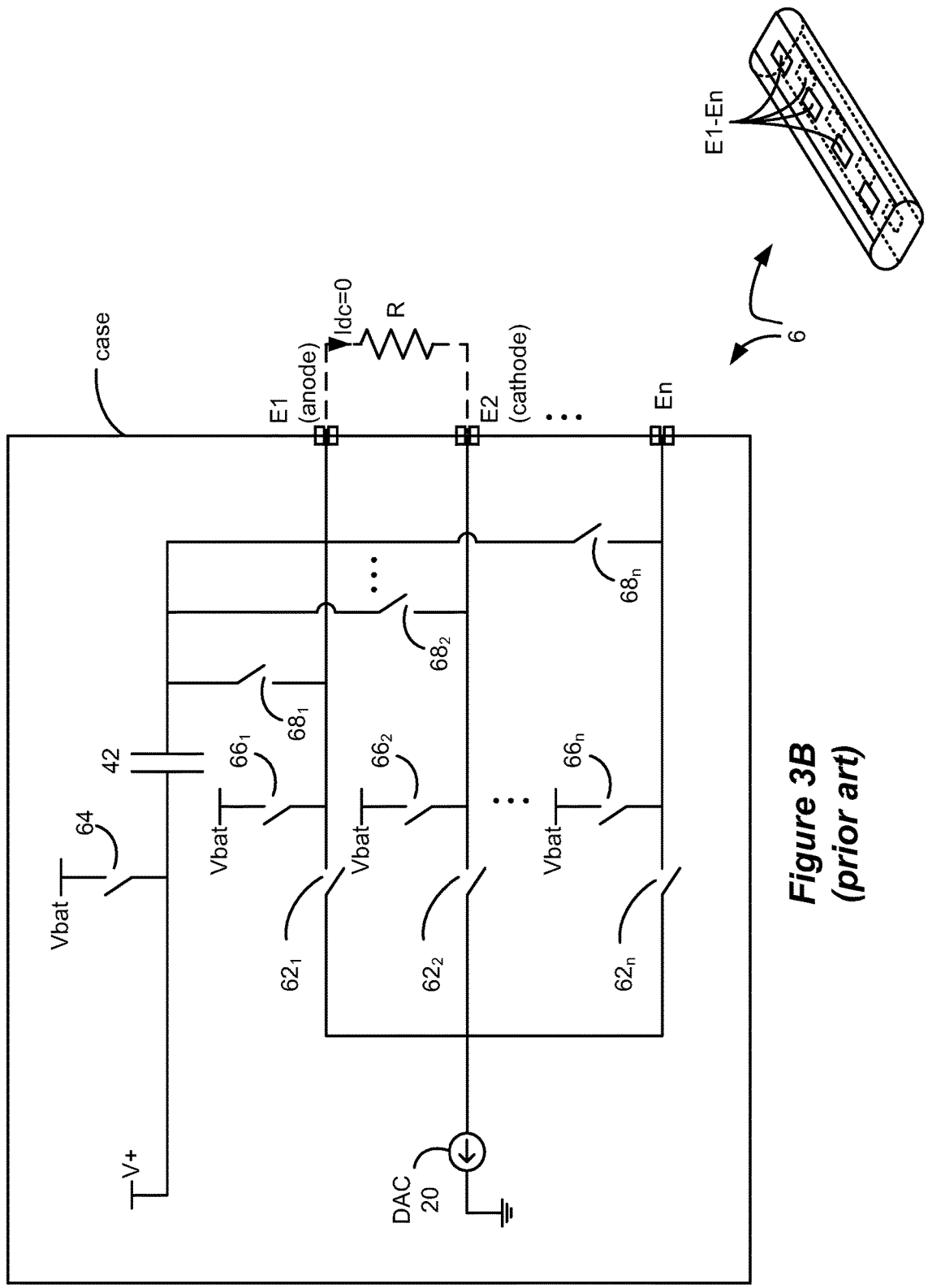

Stimulators 100 and 100' comprises N electrodes, E1-En. In the configurations shown, any one of the electrodes can be programmed as the anode, and one or more of the other electrodes can be programmed as cathodes. As best shown in FIGS. 7B and 8B, any of the electrodes E1-En can be programmed as the anode via selection of its corresponding anode selection switch $68_1$-$68_n$. However, it is not important to the invention that the anode electrode be programmable. Instead, a dedicated anode electrode, similar to microstimulator 4 shown in FIG. 3A, could also be used.

Recovery switches 64 and 66a-66x are shown in FIGS. 7B and 8B for completeness. However, because the operation of such recovery circuitry is essentially similar to that discussed earlier, and is not required in embodiments of the invention, such circuitry is not again discussed.

In the both of stimulators 100 and 100', there are X DACs 20a-20x, and X switch matrices 81a-x for coupling those DACs to any of the electrodes E1-En. Each switch matrix 81 comprises N cathode selection switches $62_{1-n}$ to couple a given DAC 20 to any of the N electrodes. For example, if it was desired to couple DAC 20b to electrode E1, thus designating electrode E1 as a cathode, then selection switch $62b_1$ in switch matrix 81b would be selected.

Figure 4:
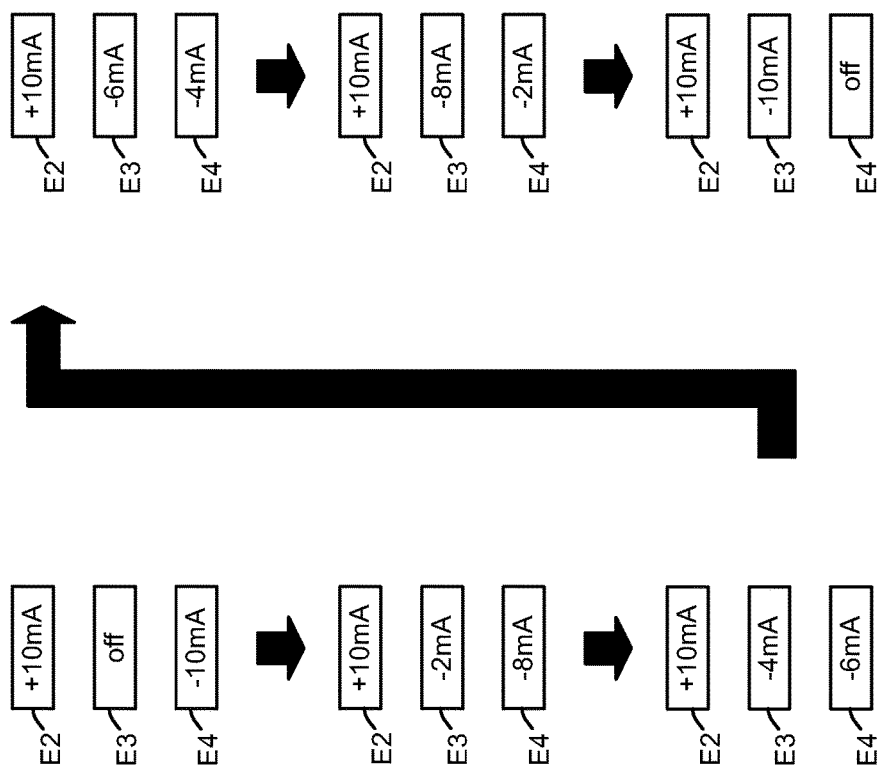
FIG. 4 illustrates the concept of current steering between electrodes in a multi-electrode stimulator device.
Figure 5:
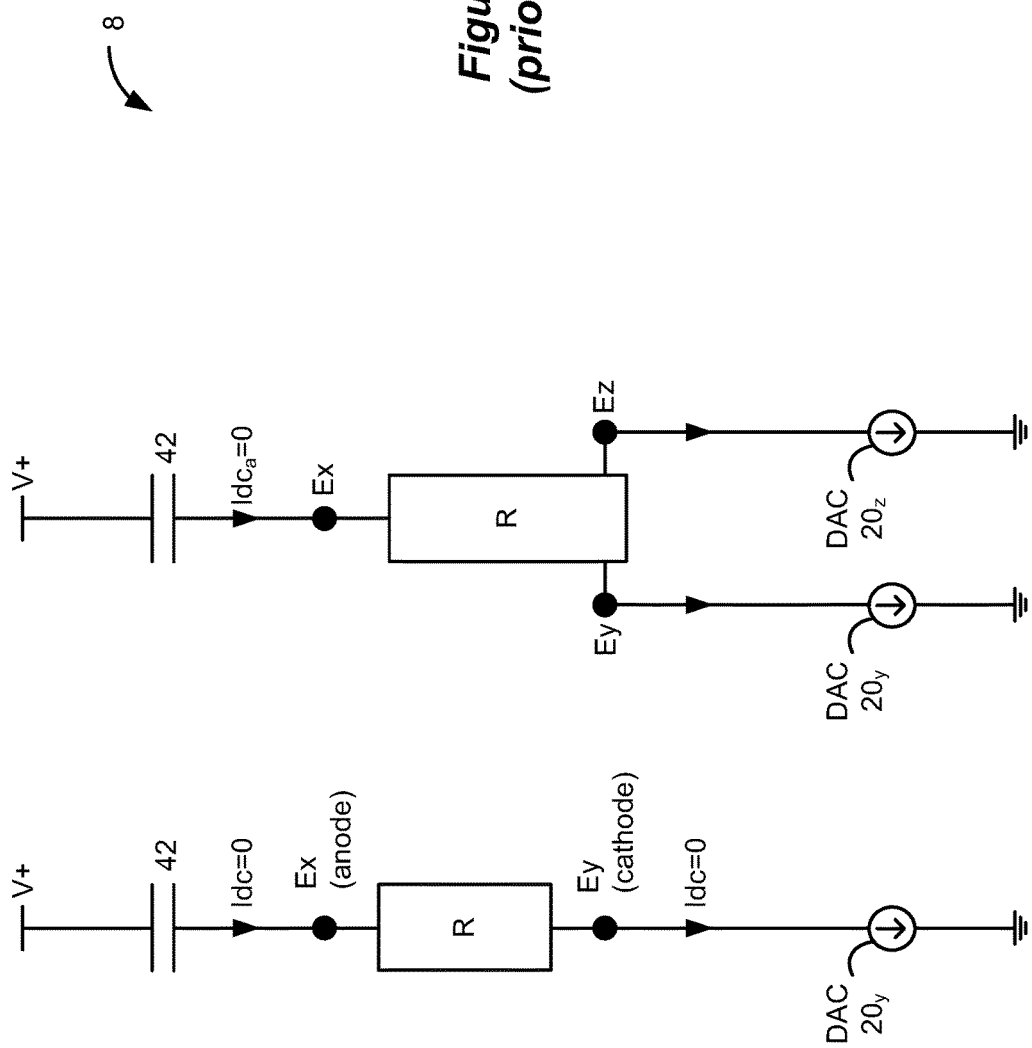
FIG. 5 illustrates DC current injection while steering the multi-electrode microstimulator of FIG. 3C.

Because there are X DACs 20a-20x, a maximum of X electrodes can act as cathodes at any given time. (Actually, it is possible that more than X electrodes can act as cathodes so long as some of these cathodes share one of the DACs, but this possibility is not further discussed). Moreover, the current at each of those X cathode electrodes can be individually and simultaneously controlled. It would normally be the case that X (the number of DACs, or the maximum number of cathodes) is smaller than N (the number of electrodes). This is true because it is generally only desired to allow some subset of the electrodes (as opposed to all electrodes) act as cathodes at a given time. For example, in a microstimulator having N=8 electrodes, it might be desirable to at most designate X=3 cathodes at one time. In an even simpler example illustrated in FIG. 8D, which presents an implementation of stimulator 100', there are N=4 electrodes and X=2 DACs. This allows one electrode to operate as the anode, while at most two electrodes can operates as cathodes. In any event, because of the use of X individually-controllable DACs 20, current in the improved stimulator 100 can be steered, such as was illustrated in FIG. 4. As noted earlier, current steering is a useful feature in an implantable stimulator.

Figure 3C:
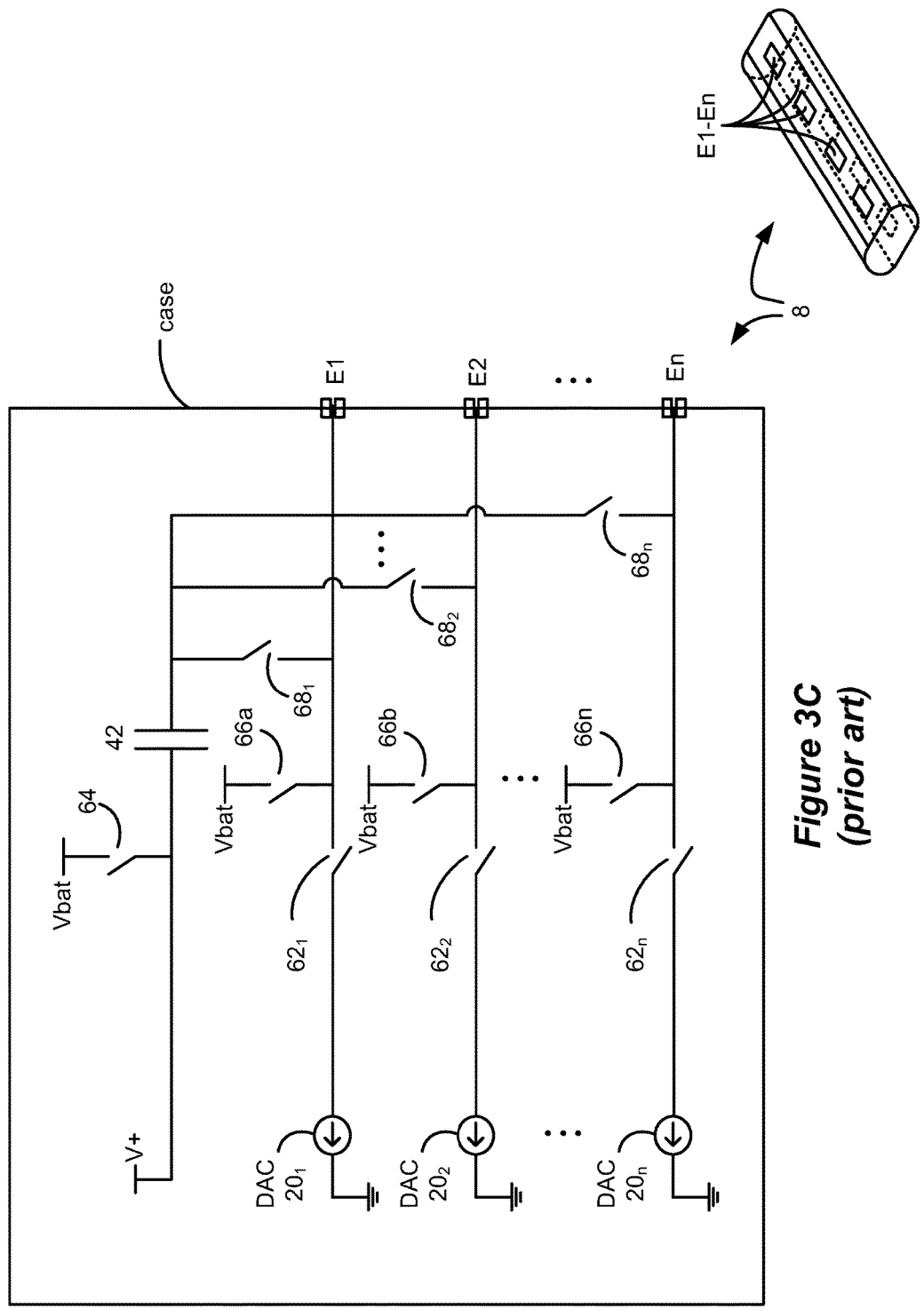

Unlike the microstimulator 8 of FIG. 3C, such steering can occur safely in stimulators 100 and 100' with no DC current injection into the patient's tissue R. Even further, and unlike the SCS 10 of FIG. 6, such safety is achieved by using a minimal number of decoupling capacitors.

Specifically, in each of stimulators 100 and 100', only X decoupling capacitors (i.e., equal to the number of DACs) are required to ensure no DC current injection. In the improved stimulator 100 of FIGS. 7A and 7B, there are no capacitors in the anode path, and X capacitors 44a to 44x in the cathode paths. In the improved stimulator 100' of FIGS. 8A and 8B, there is one capacitor 42 in the anode path, and X−1 capacitors 44a to 44(x−1) in the cathode paths. Again, because X is usually less than N, this cuts the total number of decoupling capacitors down from N to X when compared to the approach of FIG. 6 for example.

Even when only X total capacitors are used, the improved stimulators 100 and 100' guarantee no DC current injection in any path, even during current steering. This can be noticed from the different scenarios illustrated in FIGS. 7C and 8C for stimulators 100 and 100' respectively.

Figure 7C:
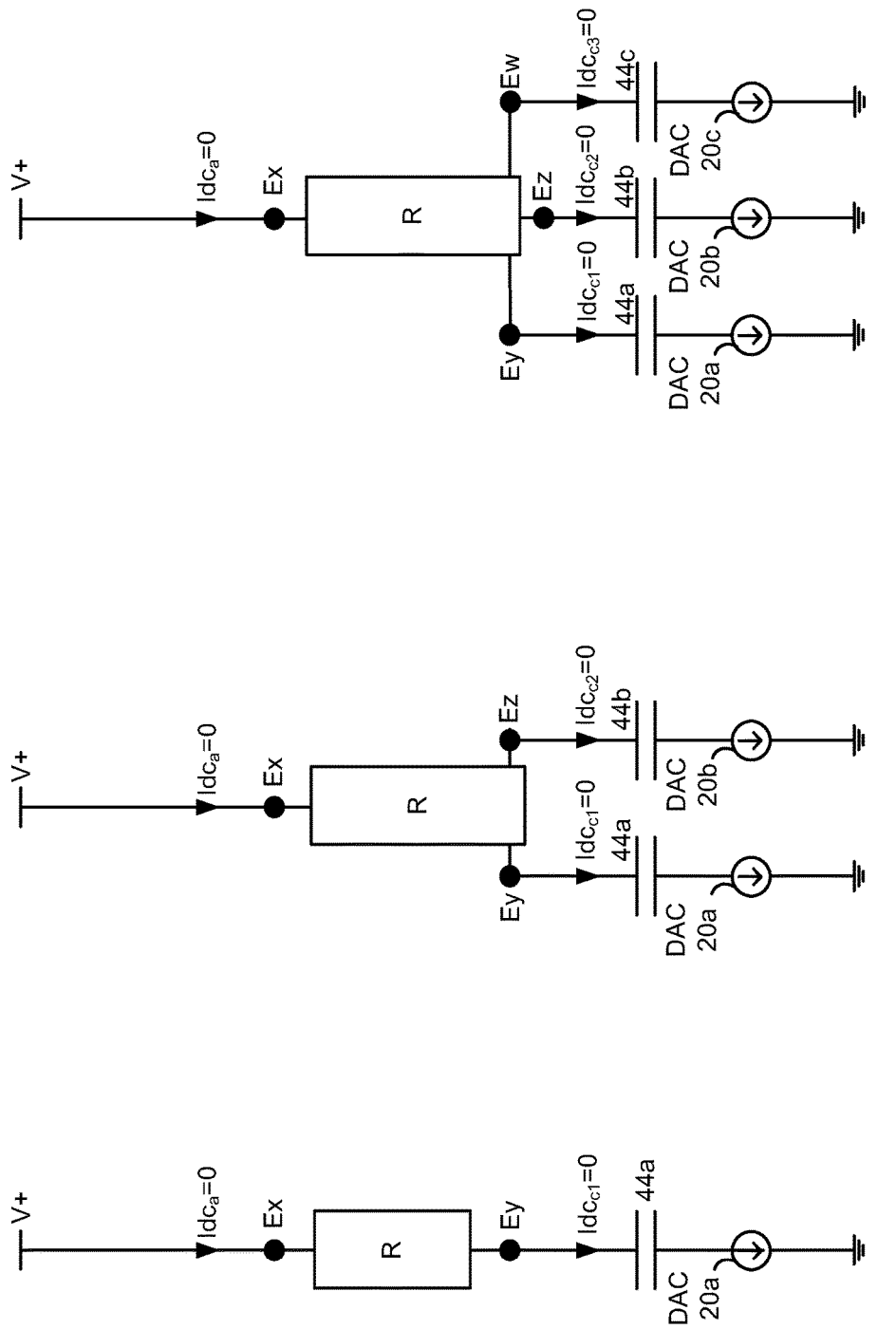

Starting with stimulator 100 and FIG. 7C, Scenario I shows selection of a single cathode electrode Ey using DAC 20a having a decoupling capacitor 44a. In this case, the cathode capacitor 44a prevents DC current injection at electrode Ey ($Idc_{c1}$=0). Because the sum of the DC currents must equal 0 at the common node established by the patent's tissue R, then the current in the anode path at electrode Ex (Idea) must also equal 0, even though the anode path lacks a capacitor.

Scenarios II and III include the selection of additional cathode electrodes, such that, generically speaking, one anode and Y cathodes are simultaneously designated as a given time. However, because each of the cathode paths includes a capacitor, and hence draws no DC current, then the current in the single anode path (Idea) must again equal 0.

In stimulator 100' of FIGS. 8A and 8B, because only X−1 decoupling capacitors are in the cathode current paths, one of the DACs (e.g., 20x) is not coupled to a capacitor. However, because stimulator 100' also includes a capacitor 42 in the anode path, the lack of a capacitor in the one cathode path does not raise concerns about DC current injection, even during current steering.

Figure 8C:
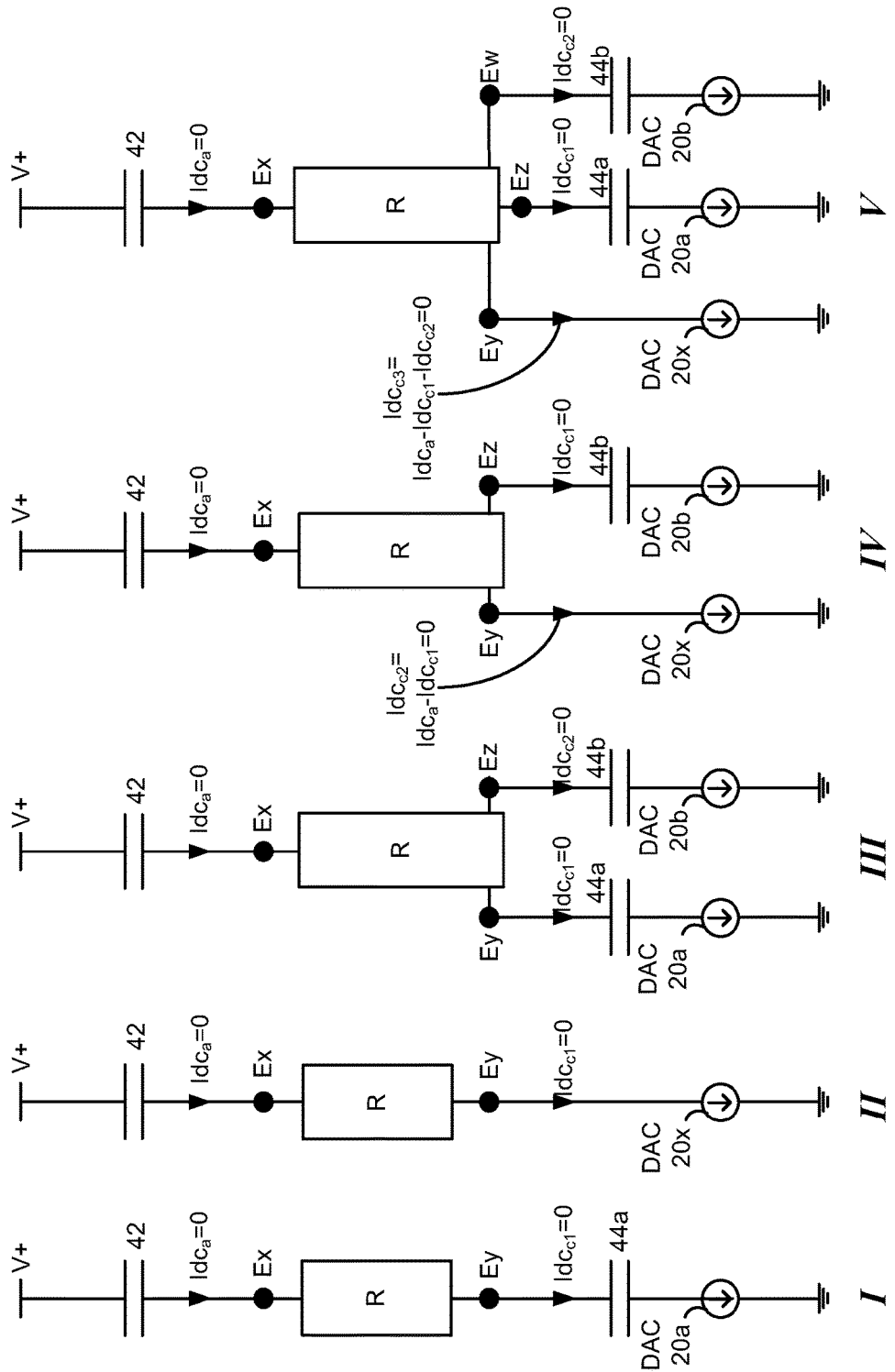
Figure 8D:
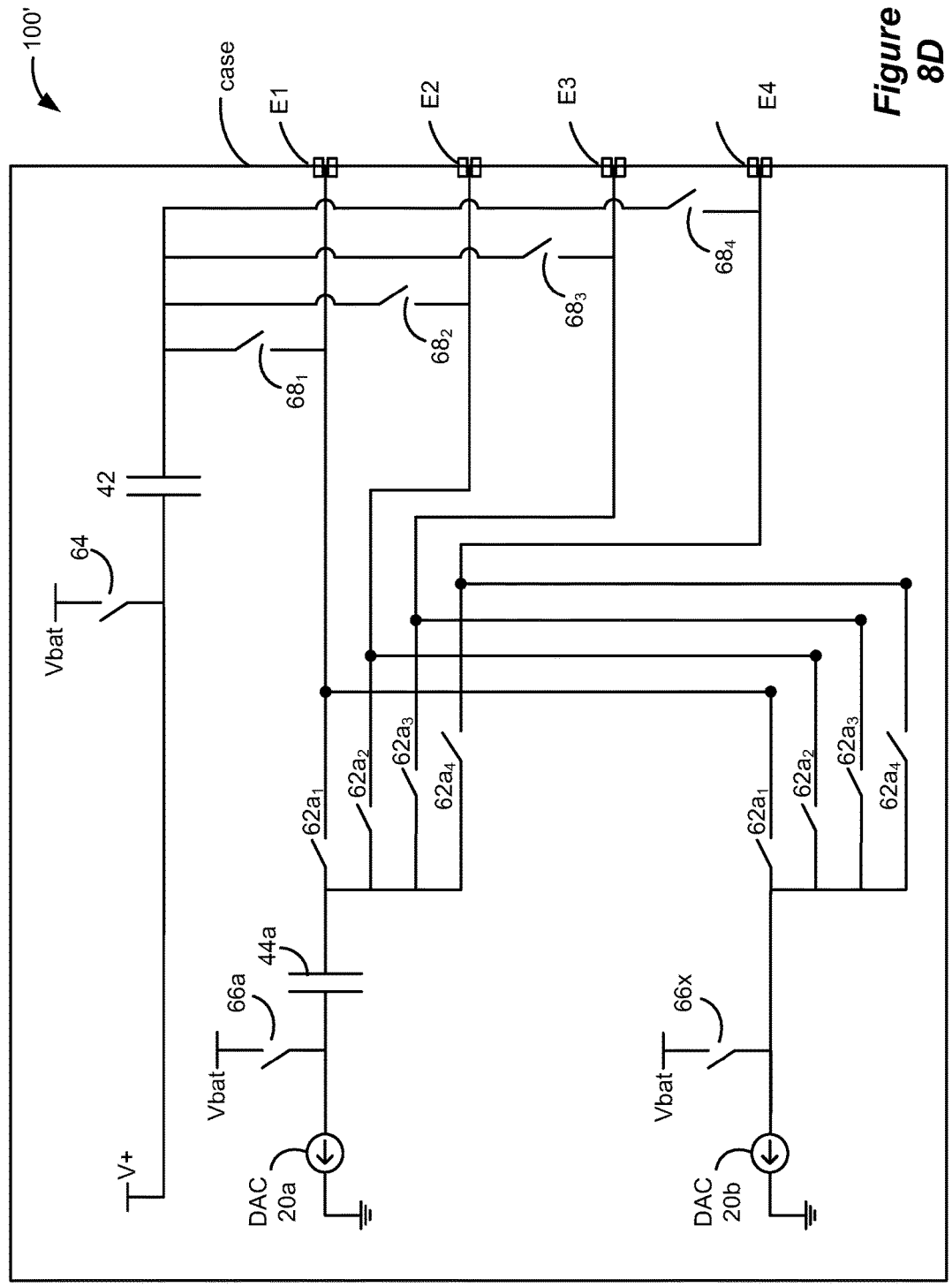

This can be noticed from the different scenarios illustrated in FIG. 8C. Scenario I shows selection of a single cathode electrode Ey using DAC 20a having a decoupling capacitor 44a. In this case, both the anode capacitor 42 and the cathode capacitor 44a prevent DC current injection along the singular current path established. Scenario II shows selection of a single cathode electrode Ey using DAC 20x that does not have a decoupling capacitor. In this case, the anode capacitor 42 prevents DC current injection along the singular current path established.

Scenarios III to V illustrates the selection of additional cathode electrodes, such that, generically speaking, one anode and Y cathodes are simultaneously designated as a given time. Scenarios III and IV select two cathode electrodes Ey and Ez as cathodes, which could be a permanent therapy setting for a given patient or could be a temporary setting such as occurs during current steering between electrodes. In Scenario III, DACs 20a and 20b are used, each having a capacitor 44a and 44b. As capacitors are present in the anode path and both cathode paths, it is elementary that no DC current injection is possible. In scenario IV, DAC 20x, which lacks a capacitor, is used, along with DAC 20b, which includes a capacitor 44b. In this case, the DC current in the anode path is $Idc_a$=0 by virtue of anode capacitor 42. The DC current in the cathode path established by DAC 20b is $Idc_{c1}$=0 by virtue of cathode capacitor 44b. Because the sum of the DC currents must equal 0 at the common node established by the patent's tissue R, the DC current in the cathode path established by DAC 20x (Idea) is 0, even though that path lacks a decoupling capacitor. Scenario V furthers this example by the addition of yet another cathode path, but still the DC current in the cathode path established by DAC 20x ($Idc_{c3}$) is 0.

To summarize, in stimulator 100', the cathode path established by DAC 20x need not contain a decoupling capacitor because all other paths to the patient's tissue R, i.e., the anode path and all other cathode paths, will contains a decoupling capacitor. Therefore, the circuitry is guaranteed to have no DC current injection into the patient's tissue, despite the lack of a decoupling capacitor in DAC 20x's cathode path.

Figure 9:
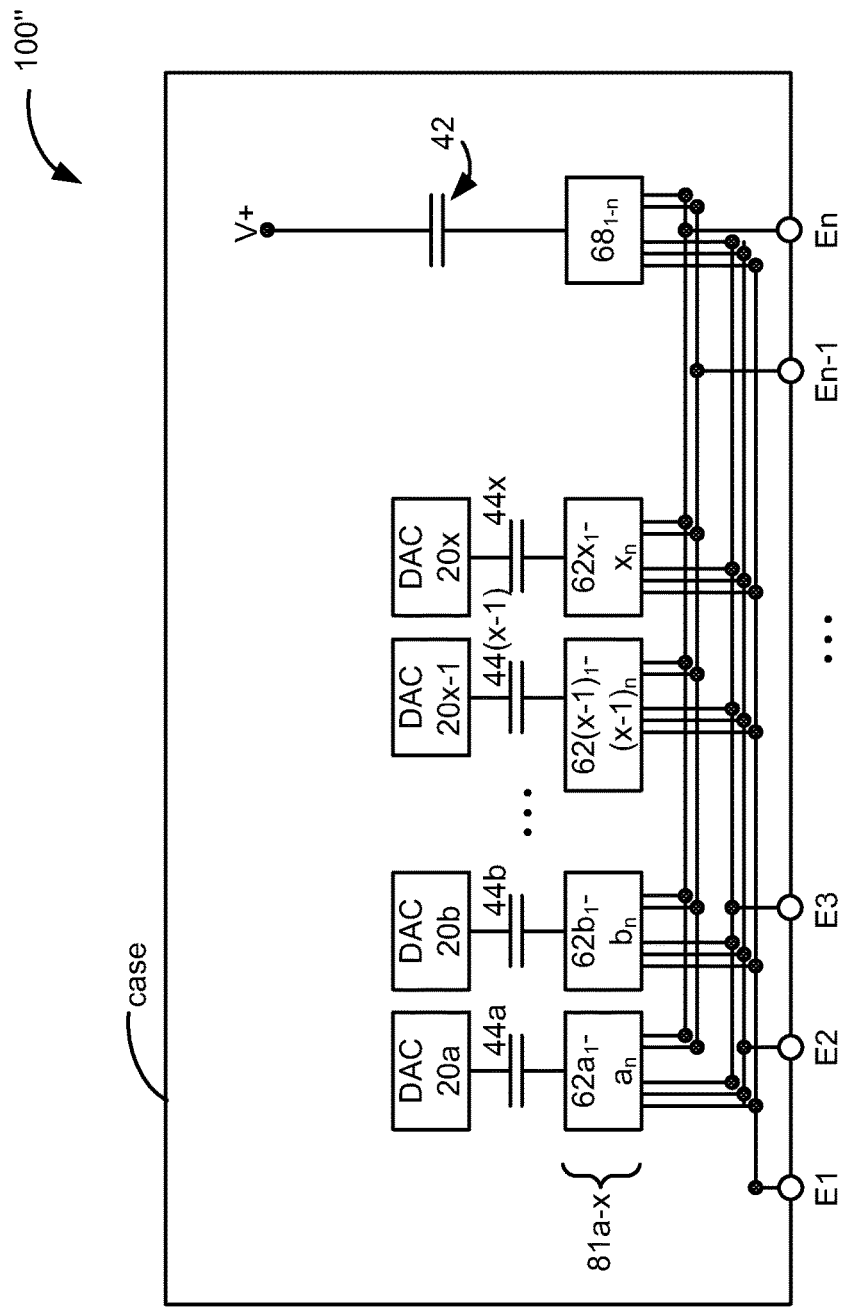
FIG. 9 illustrates a modification to the single anode/multiple cathode stimulators having one additional decoupling capacitor.

While there is a size benefit to using only X capacitors, it should be noted that X+1 capacitors can also be used in another embodiment, such as stimulator 100" shown in FIG. 9. In this embodiment, there is one capacitor 42 in the anode path, and X capacitors 44a to 44x in the cathode paths. Although stimulator 100" contains one additional capacitor when compared with stimulators 100 and 100', it can still result in a smaller number of capacitors than in previous approaches requiring N capacitors, i.e., X+1 can still be significantly less than N. For example, consider the example discussed earlier of a microstimulator having N=8 electrodes with X=3 cathode electrodes activatable at one time. Regardless of whether 3 (X) or 4 (X+1) capacitors are used, the total number is still significantly less than 8 (N), resulting in substantial space savings.

Figure 10:
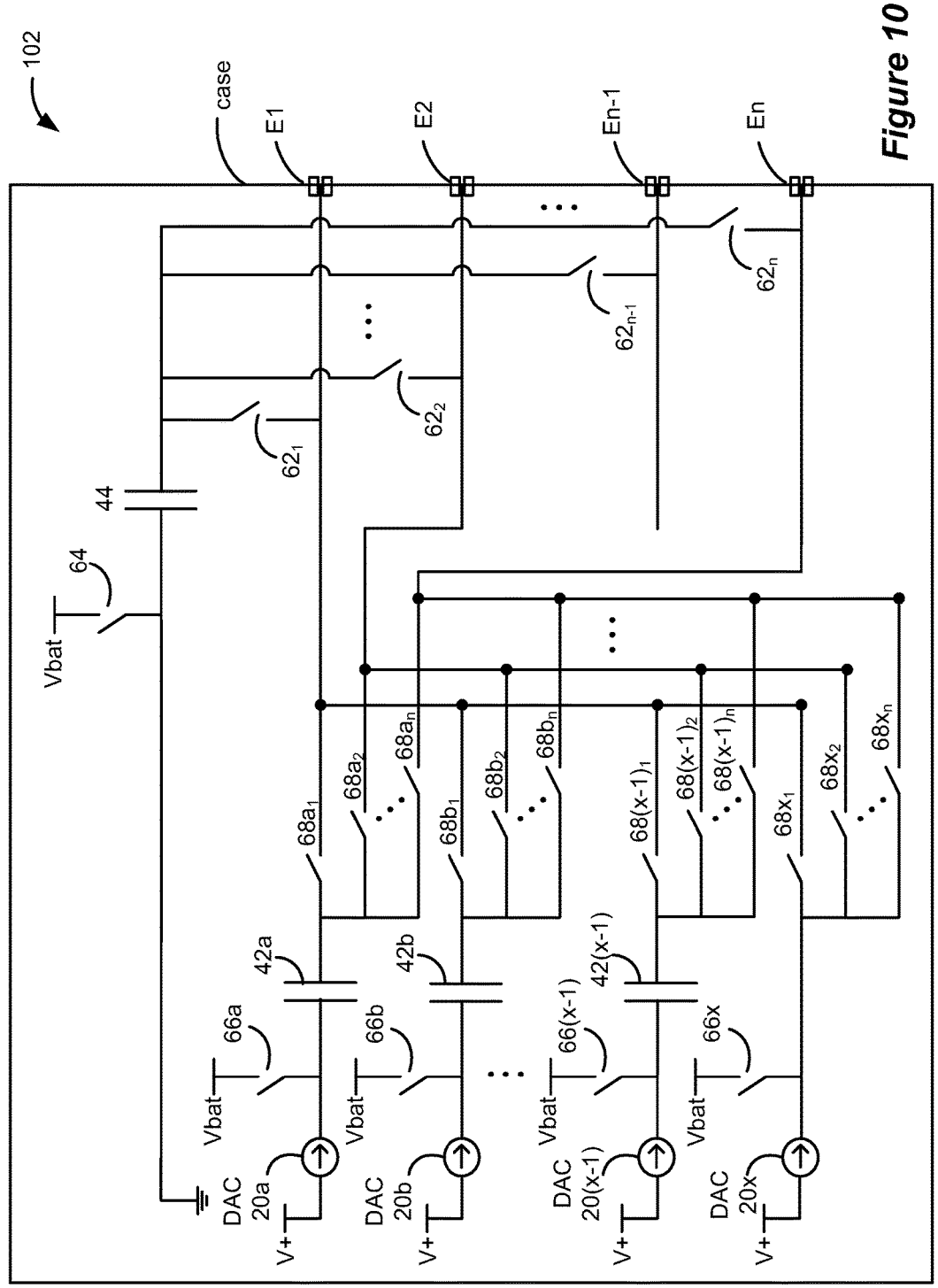
FIG. 10 illustrates implementation of the invention in a single cathode/multiple anode configuration.

To this point in the disclosure, it has been assumed that the improved stimulators 100 or 100' comprise a single anode/multiple cathode design. However, and as shown in FIG. 10, either of these embodiments can also be implemented in a multiple anode/single cathode design. FIG. 10 shows a multiple anode/single cathode stimulator 102 modeled after stimulator 100' having a single cathode path capacitor 42 and X−1 anode path capacitors 42a to 42(x−1). In this design, the circuitry has been modified to include cathode switches $62_1$-$62_n$, which allows any one of the electrodes E1-En to function as the cathode or current sink. Multiple anodes can be selected via anode selection switches $68a_1$ to $68x_n$, which in conjunction with DACs 20a-20x can allow more than one electrode to act as an anode or current source at one time. Regardless of the cathode chosen, decoupling capacitor 44 will remain in the cathode path. Notice again that DACs 20a-20(x−1) are coupled to decoupling capacitors 42a to 42(x−1), while the anode path containing DAC 20x contains no decoupling capacitor. However, for the same reasons discussed above, such architecture still guarantees no DC current injection, and is safe in this respect.

To this point in the disclosure, embodiments of the invention have been illustrated in either single anode/multiple cathode or multiple anode/single cathode configurations. However, the invention is also extendable to a multiple anode/multiple cathode configuration, such as is shown in stimulator 110 of FIG. 11A. As shown, separate DACs are provided to service both the anodes and the cathodes. Specifically, NDACs 20a-20i comprise current sinks and thus operate as cathode current sources, and are coupleable via cathode selection switches 62 to designate any of electrodes E1-En as cathodes. Likewise, PDACs 21a-21j comprise opposite-polarity anode current sources, and are coupleable via anode selection switches 68 to designate any of electrodes E1-En as anodes. As one skilled in the art will appreciate, reference to "N" or "P" DACs relates to the polarity of the devices preferably used in the DAC circuitry, with PDACs generally comprising P-channel transistors, and NDACs generally comprising N-channel transistors. See, e.g., U.S. Patent Application Publication 2007/0038250. As shown, there are I NDACs 20, and therefore (assuming no DAC sharing), I of the electrodes can act as cathodes at any given time. There are J PDACs 21, and therefore (again assuming no sharing), J of the electrodes can act as anodes at a given time. In this example, I+J=X, meaning (consistent with earlier examples) that there are a total of X DACs 20 or 21 and a maximum of X electrodes that can be active (I cathodes and J anodes) at one time. In a sensible application, I and J could be equal.

Multiple anode/multiple cathode stimulator 110 comprises at least X−1 decoupling capacitors. This means a decoupling capacitor can be missing from any of the X NDACs 20 or PDACs 21 illustrated, but as shown, the capacitor is missing from the anode path coupled to the last PDAC 21j. Thus, in the illustrated example, there are I cathode path capacitors, and J−1 anode path capacitors, for a total of X−1 capacitors.

Even though a capacitor is missing from PDAC 21j's anode path, the design is still guaranteed to allow no DC current injection at any electrode, because once again, the presence of capacitors in all other anode and cathode paths prevents this. The scenario illustrated in FIG. 11B shows this, and based on similar earlier illustrations, should be self explanatory. Generically, assume P electrodes can be designated as anodes, including at least electrode Ey coupled to PDAC 21j. Likewise, Q electrodes are simultaneously designated as cathodes. The result is P+Q−1 capacitors in the various paths. However, there can be no DC current injection into PDAC 21j's anode path despite the missing capacitor. Therefore, the X−1 capacitors ensure no DC current injection into the node formed by the patient's tissue R. Although the capacitor is shown as missing in an anode path, the capacitor may also be missing from one of the cathode paths to the same effect.

Figure 11A:
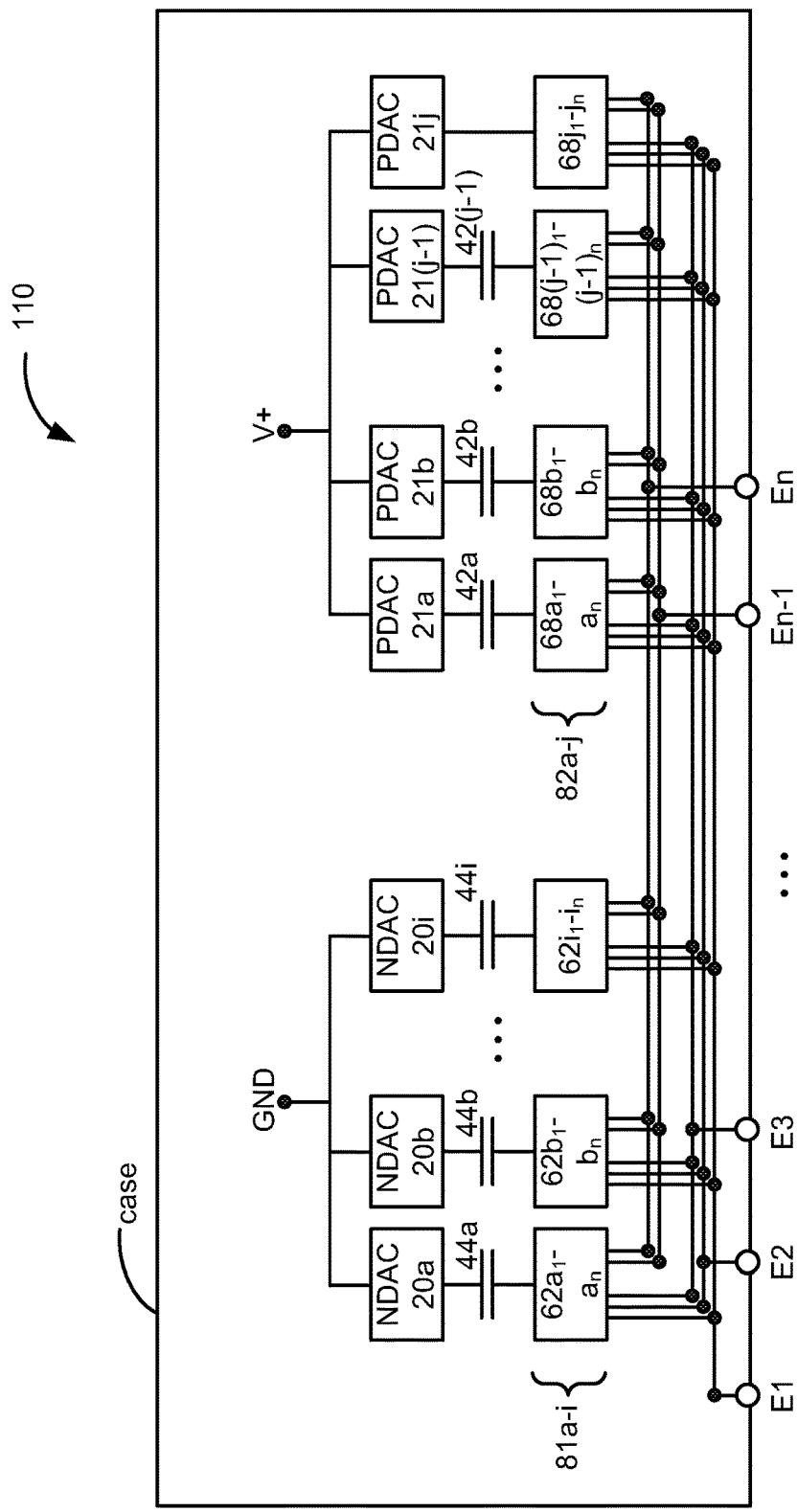
FIGS. 11A and 11B illustrate implementation of the invention in a multiple anode/multiple cathode configuration having a minimal number of decoupling capacitors.
Figure 11B:
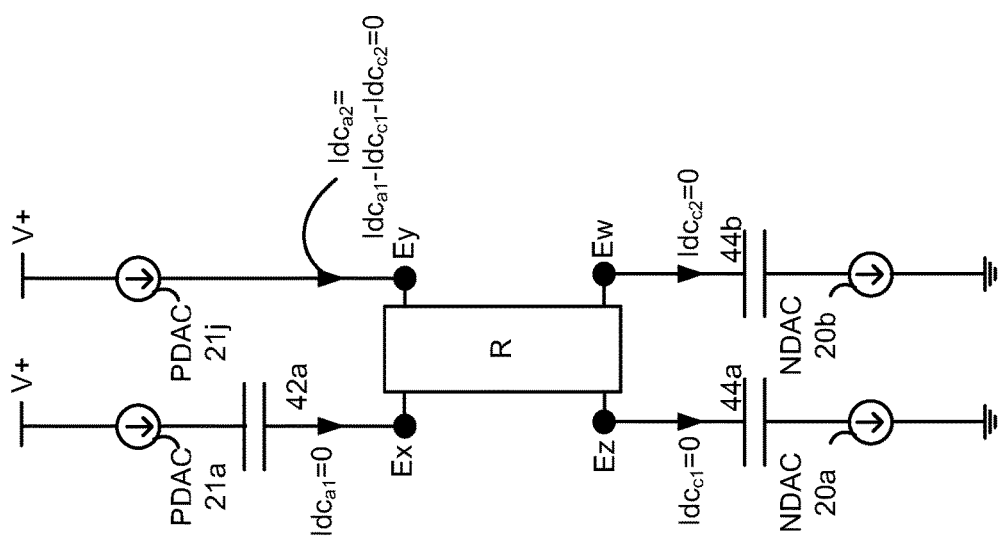

Because only X−1 decoupling capacitors are required in the stimulator 110 of FIG. 11A, and because X can normally be made smaller than the total number of electrodes N, stimulator 110 can be made smaller than approaches requires N decoupling capacitors (see, e.g., FIG. 6). For example, consider a spinal cord stimulator having N=16 electrodes, and which has three NDACs 20 and three PDACs 21, meaning that a total of X=6 electrodes (I=3 anodes, J=3 cathodes) can be activated at any given time. Such a design would require only X−1=5 decoupling capacitors instead of 16 as had been typical in previous spinal cord stimulator designs.

Figure 12:
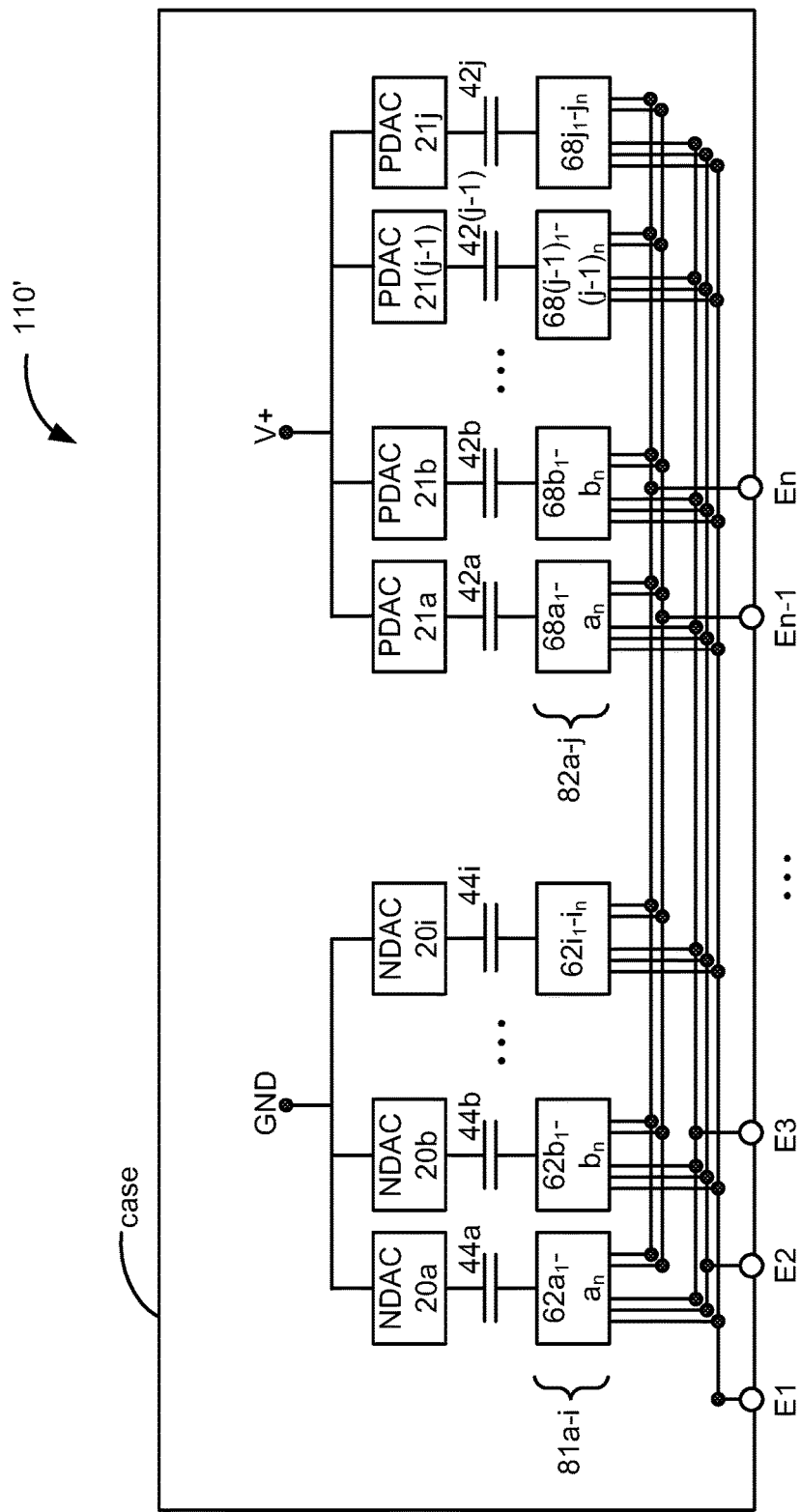
FIG. 12 illustrates a modification to the multiple anode/multiple cathode stimulator of FIG. 11A having one additional decoupling capacitor.

FIG. 12 illustrates a modification to the embodiment of stimulator 110 of FIG. 11A in which no decoupling capacitor is missing from any of the anode or cathode paths. Although this stimulator 110' requires one additional capacitor compared to stimulator 110 (X versus X−1), it can still result in a substantial reduction in the number of capacitors required. For example, and continuing the example above, the number of capacitors in a spinal cord stimulator could be cut from 16 to six for example.

Figure 13:
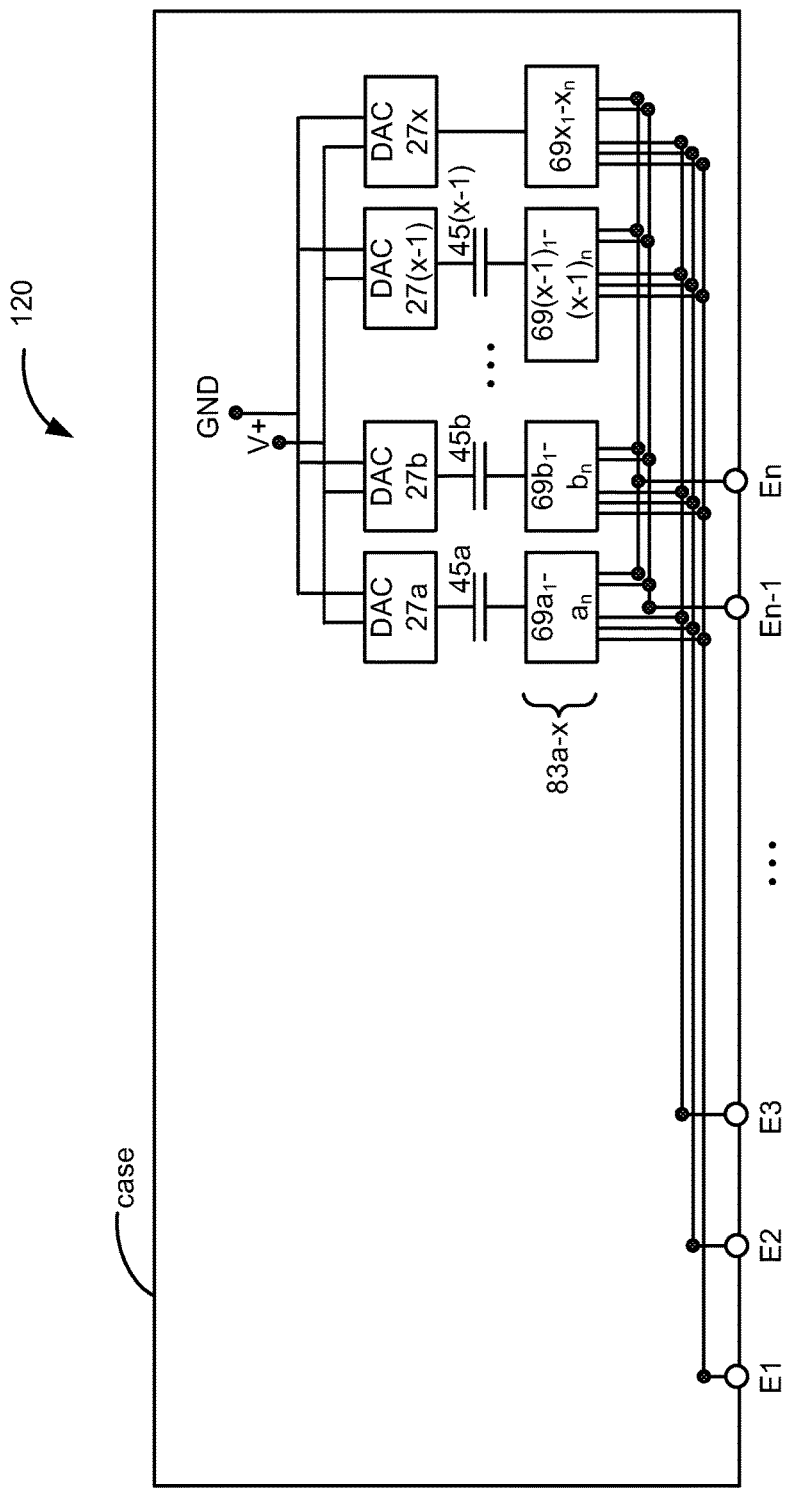
FIG. 13 illustrates another implementation of the invention in a multiple anode/multiple cathode configuration having a minimal number of decoupling capacitors.

FIG. 13 illustrates yet another multiple anode/multiple cathode stimulator 120. In comparison to stimulator 110 of FIG. 11A which was implemented using discrete NDACs and PDAC, stimulator 120 comprise X generic DACs 27a-x. DACs 27a-x are programmable to operate either as cathode (sink) current sources or anode (source) current sources, and therefore may comprise a combination of known NDAC and PDAC circuitry. DACs 27a-x are coupleable to any of the N electrodes by switch matrices 83a-x. Because the DACs 27a-x are programmable to either sink or source current, the selection switches 69 in each of the switch matrices 83 may be implementable as transmission gates having both P and N channel transistors which can pass the sourced or sunk current with equal efficiency. The X DACs 27a-x permit X of the electrodes can act as cathodes or anodes at any given time. More specifically, because there must be at least one cathode and anode at any given time, there can be M cathodes and X-M anodes active at any given time, which M is a positive integer.

Like stimulator 110, multiple anode/multiple cathode stimulator 120 comprises at least X−1 decoupling capacitors, as shown in FIG. 13. This means a decoupling capacitor 45 can be missing from any of the X DACs 27 illustrated, but as shown, the capacitor is missing from the current path coupled DAC 27x. Even though a capacitor is missing from DAC 27x's current path, the design is still guaranteed to allow no DC current injection at any electrode, because once again, the presence of capacitors in all other current paths prevents this. To summarize, because the X−1 capacitors prevent DC current injection into the node formed by the patient's tissue R, there can be no DC current injection into PDAC 27x's current path despite the missing capacitor. As with earlier embodiments, because only X−1 decoupling capacitors are required, stimulator 120 can generally be made smaller, etc.

Figure 14:
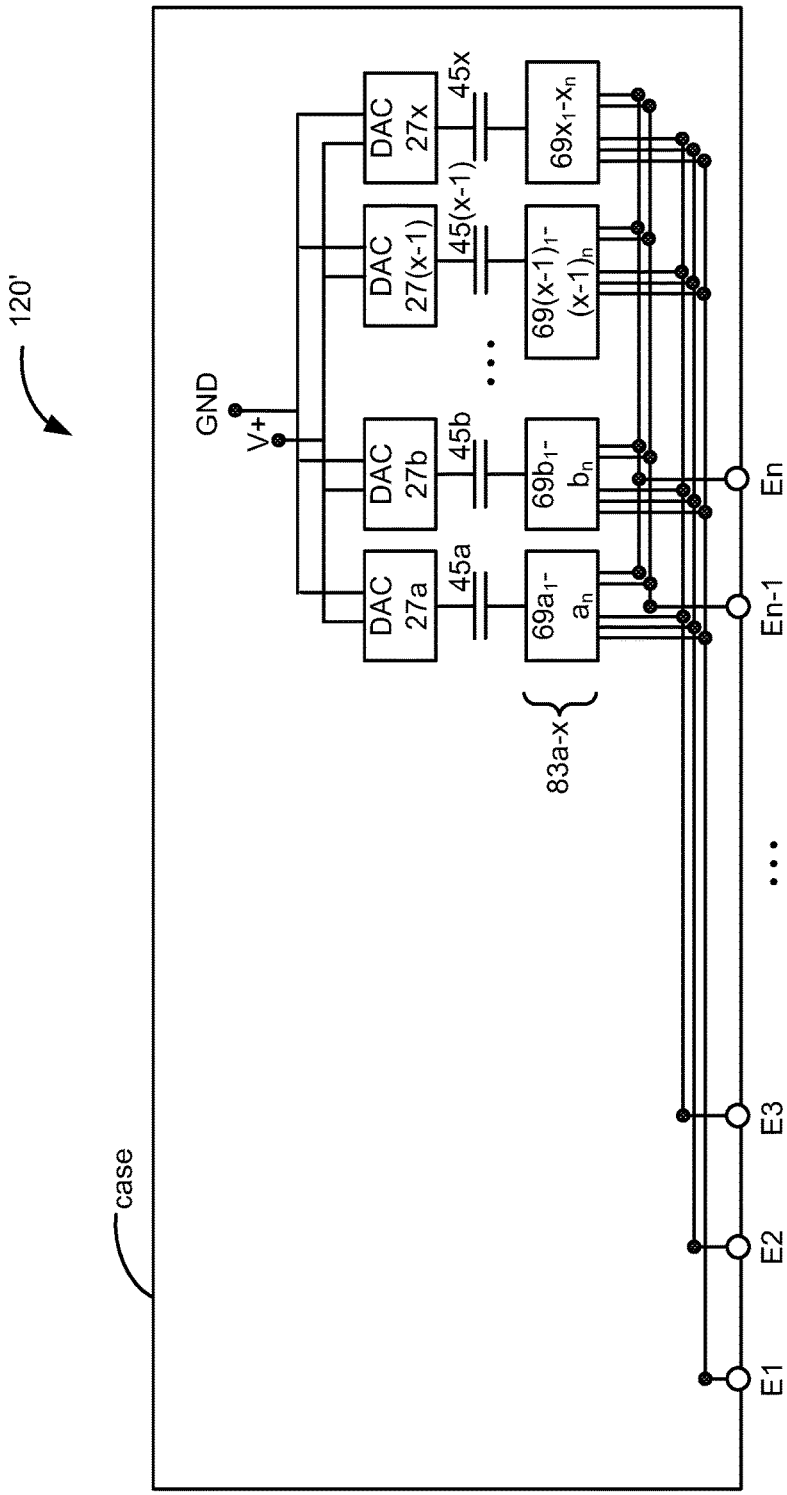
FIG. 14 illustrates a modification to the multiple anode/multiple cathode stimulator of FIG. 13 having one additional decoupling capacitor.

FIG. 14 illustrates a modification to the embodiment of stimulator 120 of FIG. 13 in which no decoupling capacitor is missing from any of the current paths. Although this stimulator 120' requires one additional capacitor compared to stimulator 120 (X versus X−1), it can still result in a substantial reduction in the number of capacitors required.

The disclosed stimulators improves upon the prior art. Because they contains a smaller number of DACs (X) relative to the number of electrodes (N), and accordingly contains a smaller number of decoupling capacitors (either X−1, X, or X+1 depending on the embodiment considered), the stimulator can be incorporated into a relatively small case. This facilitates use as a multi-electrode microstimulator for example, or allows a spinal cord stimulator case to be made that much smaller. Moreover, the disclosed designs guarantee no DC current injection, even during current steering, i.e., during the simultaneous activation of more than one cathode and/or more than one anode.

This disclosure has referred to "anodes" as being sources of current and "cathodes" as sinks of current. However, because this designation is relative, an "anode" can also refer to a sink of current and a "cathode" can also refer to a source of current. Therefore, as used herein, "anode" and "cathode" should simply be understood as having opposite polarities.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. An implantable medical device, comprising:
an electrode array comprising a plurality of electrodes;

a first current path coupleable to a first of the plurality of electrodes, wherein the first current path comprises an anode or cathode current path;

a plurality of second current paths each coupleable to a different second of the plurality of electrodes, wherein each of the second current paths comprises the other of an anode or cathode current path when compared to the first current path, at least one current source configured to provide a current in one of the second current paths;

wherein the first current path and the second current paths together comprise X current paths; and a plurality of X−1 capacitors, wherein one of the X−1 capacitors is placed in one of the X current paths such that only one of the X current paths does not include a capacitor.

2. The device of claim 1, wherein one of the X−1 capacitors is placed in each of the second current paths such that only the first current path does not include a capacitor.

3. The device of claim 1, wherein one of the X−1 capacitors is placed in the first current path, and one of the remaining X−1 capacitors is placed in some of the second current paths such that only one of the second current paths does not include a capacitor.

4. The device of claim 1, wherein the device comprises a plurality of current sources, wherein the first current path and each second current path comprises one of the current sources.

5. The device of claim 1, wherein the device comprises a plurality of current sources, wherein each second current path comprises one of the plurality of current sources.

6. The device of claim 1, wherein the device comprises a plurality of current sources, further comprising a switch matrix, wherein the switch matrix is configured to include any of the current sources in each of the second current paths.

7. The device of claim 1, further comprising a switch matrix, wherein the switch matrix is configured to include the at least one current source in each of the second current paths.

8. The device of claim 1, wherein the first current path is connected to a reference voltage and does not contain a current source.

9. The device of claim 1, wherein if one of the X−1 capacitors is placed in a second current path, it is placed between the at least one current source and the second of the plurality of electrodes in that second current path.

10. An implantable medical device, comprising:
an electrode array comprising a plurality of electrodes;
a plurality of first current paths each coupleable to a different one of the plurality of electrodes, wherein each of the first current paths comprises an anode current path;
a plurality of second current paths each coupleable to a different one of the plurality of electrodes, wherein each of the second current paths comprises a cathode current path,
at least one anodic current source configured to provide a current in one of the first current paths;
at least one cathodic current source configured to provide a current in one of the second current paths;
wherein the first current paths and the second current paths together comprise X current paths; and
a plurality of X−1 capacitors, wherein one of the X−1 capacitors is placed in one of the X current paths such that only one of the X current paths does not include a capacitor.

11. The device of claim 10, wherein one of the X−1 capacitors is placed in each of the second current paths such that only one of the first current paths does not include a capacitor.

12. The device of claim 10, wherein one of the X−1 capacitors is placed in each of the first current paths such that only one of the second current paths does not include a capacitor.

13. The device of claim 10, wherein the device comprises a plurality of anodic current sources and a plurality of cathodic current sources, wherein each first current path comprises an anodic current source, and each second current path comprises a cathodic current source.

14. The device of claim 10, wherein the device comprises a plurality of anodic current sources, further comprising a first switch matrix, wherein the first switch matrix is configured to include any of the first current sources in each of the first current paths.

15. The device of claim 14, wherein the device comprises a plurality of cathodic current sources, further comprising a second switch matrix, wherein the second switch matrix is configured to include any of the second current sources in each of the second current paths.

16. The device of claim 10, further comprising a first switch matrix, wherein the first switch matrix is configured to include the at least one anodic current source in each of the first current paths, and further comprising a second switch matrix, wherein the second switch matrix is configured to include the at least one cathodic current source in each of the second current paths.

17. The device of claim 10, wherein the at least one anodic current source is connected to a compliance voltage, and wherein the at least one cathodic current source is connected to ground.

18. An implantable medical device, comprising:
an electrode array comprising a plurality of electrodes;
at least one current source configured to provide a current to one of X current paths connected to each electrode;
a switch matrix in each one of the X current paths, wherein each switch matrix is configured to connect any of the plurality of electrodes to the at least one current source; and
a plurality of X−1 capacitors, wherein one of the X−1 capacitors is placed in one of the X current paths such that only one of the X current paths does not include a capacitor.

19. The device of claim 18, wherein if one of the X−1 capacitors is placed in one of the X current paths, it is placed between the at least one current source and the electrode in that current path.

20. The device of claim 18, wherein the device comprises a plurality of current sources, wherein the switch matrix is configured to connect any of the current sources to each of the electrodes.

* * * * *